United States Patent
Wen et al.

(10) Patent No.: US 9,051,584 B2
(45) Date of Patent: Jun. 9, 2015

(54) HEAT-RESISTANT NEWCASTLE DISEASE VIRUS LIVE VACCINE VECTOR SYSTEM AND USE THEREOF

(71) Applicant: Institute of Animal Husbandry and Veterinary Science, Hubei Academy of Agricultural Sciences, Wuhan (CN)

(72) Inventors: Guoyuan Wen, Wuhan (CN); Huabin Shao, Wuhan (CN); Jun Yang, Wuhan (CN); Honglin Wang, Wuhan (CN); Qingping Luo, Wuhan (CN); Rongrong Zhang, Wuhan (CN); Diyun Ai, Wuhan (CN); Ling Luo, Wuhan (CN); Yu Shang, Wuhan (CN); Jing Guo, Wuhan (CN); Chen Chen, Wuhan (CN)

(73) Assignee: INSTITUTE OF ANIMAL HUSBANDRY AND VETERINARY SCIENCES, HUBEI ACADEMY OF AGRICULTURAL SCIENCES, Wuhan, Hubei (CN)

( * ) Notice: Subject to any disclaimer, the term of this patent is extended or adjusted under 35 U.S.C. 154(b) by 0 days.

(21) Appl. No.: 13/924,812

(22) Filed: Jun. 24, 2013

(65) Prior Publication Data
US 2014/0287496 A1    Sep. 25, 2014

(30) Foreign Application Priority Data
Mar. 20, 2013    (CN) .......................... 2013 1 0090099

(51) Int. Cl.
*C12N 15/86* (2006.01)
*C12N 7/00* (2006.01)

(52) U.S. Cl.
CPC *C12N 15/86* (2013.01); *C12N 7/00* (2013.01); *C12N 2760/18121* (2013.01); *C12N 2760/18122* (2013.01); *C12N 2760/18143* (2013.01); *C12N 2760/18151* (2013.01)

(58) Field of Classification Search
None
See application file for complete search history.

(56) References Cited

U.S. PATENT DOCUMENTS

2002/0173038 A1* 11/2002 Morgan et al. ................ 435/456
2004/0235134 A1* 11/2004 Peeters et al. ............. 435/235.1
2008/0031895 A1*  2/2008 Galarza et al. ............ 424/209.1

OTHER PUBLICATIONS

Kattenbelt et al., Genome sequence of the thermostable Newcastle disease virus (strain 1-2) reveals a possible phenotypic locus; Veterinary Microbiology, vol. 114, pp. 134-141, 2006.*
Guoyuan Wen et al., "Complete genome sequence and molecular characterization of thermostable Newcastle disease virus strain TS09-C", Virus Genes, 2013,542-545.

* cited by examiner

*Primary Examiner* — Jennifer Dunston
*Assistant Examiner* — Addison D Ault
(74) *Attorney, Agent, or Firm* — Tim Tingkang Xia, Esq.; Morris, Manning & Martin, LLP

(57) ABSTRACT

A heat-resistant NDV live vaccine vector system includes a transcription plasmid, three helper plasmids, and host cells. The transcription plasmid is constructed by through cloning complete genomic cDNA of a heat-resistant NDV vaccine strain to a pBR322 vector. The three helper plasmids are constructed by cloning sequences coding nucleoprotein (NP), phosphoprotein, large polymerase protein of a heat-resistant NDV vaccine strain respectively to pcDNA3.1 vectors. A recombinant NDV artificially obtained by cotransfecting host cells with the transcription plasmid and the three helper plasmids shows heat-resistance.

9 Claims, 7 Drawing Sheets

HEAT-RESISTANT NEWCASTLE DISEASE VIRUS LIVE VACCINE VECTOR SYSTEM AND USE THEREOF

CROSS-REFERENCE TO RELATED APPLICATION

This non-provisional application claims priority under 35 U.S.C. §119(a) on Patent Application No. 201310090099.4 filed in P.R. China on Mar. 20, 2013, the entire contents of which are hereby incorporated by reference.

Some references, if any, which may include patents, patent applications and various publications, may be cited and discussed in the description of this invention. The citation and/or discussion of such references, if any, is provided merely to clarify the description of the present invention and is not an admission that any such reference is "prior art" to the invention described herein. All references listed, cited and/or discussed in this specification are incorporated herein by reference in their entireties and to the same extent as if each reference was individually incorporated by reference.

FIELD OF THE INVENTION

The present invention related generally to a live virus vector system, and more particularly relates to a heat-resistant Newcastle disease virus (NDV) live vaccine vector system that is capable of producing a recombinant heat-resistant NDV live vaccine.

BACKGROUND OF THE INVENTION

Newcastle disease (ND), also referred to as Asian fowl plague, is a highly infectious devastating disease caused by NDV. With high morbidity and mortality rates, ND is listed as one of the two class A poultry diseases (the other one is avian influenza) by the Office International des Epizooties (OIE) and is a national mandatory immune disease. First breaking out in Java, Indonesia and Newcastle, England in 1926, ND among chickens has always been prevalent around the world except the Oceania, and has caused tremendous economic losses in the world. In China, ND is also one of the most destructive poultry diseases, and the disease has been prevalent in many regions in China. ND is mainly controlled through immunization and prevention. In recent years, with wide application of vaccines, large-scale outbreaks and prevalence of ND have been significantly controlled. However, due to incomplete vaccine cold chain system, inappropriate usage methods, and unscientific immunization procedures, typical and atypical NDs constantly emerge. Constant enlargement of the range of ND hosts and emergence and prevalence of mutated strains make prevention and control of ND even more complicated.

Currently, ND vaccines internationally produced and used are classified into two types, that is, live vaccines and inactivated vaccines. The live vaccines include low virulent strain vaccines and moderate virulent strain vaccines. The low virulent strain vaccines include lineage II vaccine (B1), lineage III vaccine (LaSota strain), clone 30, V4, etc., and the moderate virulent strain vaccines include lineage I vaccine, Roskin strain, Komorov strain, Hert 33 strain, Mukteswar strain, etc. Some low virulent live vaccines have a unique heat-resistant feature and are known as heat-resistant live vaccines, and representative strains thereof include V4, 1-2, HB92, and TS09-C strains. This type of vaccines has advantages of being heat-resistant, low virulent, highly effective in immunization, infectious within the group, and capable of performing immunization by multiple approaches (food mixing and spraying), and is applicable to prevent and control ND among various poultries such as chickens, pigeons, and quails. Compared with other non-heat-resistant vaccines, the vaccines are advantageous in southern areas with generally high temperatures and rural areas with poor cold chain conditions, and play an important role in preventing and controlling of the ND.

With the rapid development of molecular biology, basic molecular research on NDV progresses greatly. Genomic RNA of NDV, together with nucleoprotein (NP), phosphoprotein (P), and large polymerase protein (L) coded by the genomic RNA, form a nucleoprotein complex, which subsequently starts a first round of transcription of the RNA and translation and synthesis of virus protein. Components of the virus produce infectious progeny viruses through self-packaging. According to this principle, European scholars established the first reverse genetic manipulation system of highly pathogenic NDVs in 1999. Studies shown that exogenous reporter genes or immunogenic genes can be inserted at different sites of an NDV genome and expressed, and the NDV genome still maintains a high level of genetic and expression stability after many times of serial passage in cells or chick embryos.

Using attenuated heat-resistant NDV strains as live virus vaccine vectors, among other things, has the following prominent advantages. (1). The attenuated heat-resistant NDV strains can be preserved and transported at room temperature, which reduces dependence on the cold chain system, and the strains are more suitable for using in high temperature areas. (2). The attenuated heat-resistant NDV strains have a high group infection rate and a better immunization effect. (3). The vaccine thereof has extremely low toxicity and is not lethal to chick embryos, so that chick embryo immunization or zero-day immunization can be performed. (4). A replication process is from RNA to RNA without a DNA stage and with no possibility of integration with cell genomes. (5). Humoral immunization, mucosal immunization, and cell immunization can be induced at the same time, which produces more comprehensive immunization protection. (6). The vaccine can be provided in multiple manners, such as food mixing, water supplying, and spraying, thus is convenient to use. (7). Attenuated NDV strains have high-titer chick embryo growth and low growth cost. It is required in China to immunize newborn chicks with attenuated NDV vaccines, and at least more than one billion doses of attenuated vaccines are used each year for preventing and controlling ND. Therefore, using the attenuated heat-resistant NDV strains as live virus vaccine vectors provide tremendous economic significance.

Since the first heat-resistant NDV strain, the V4 strain, is isolated in 1966, many heat-resistant NDV strains have been obtained through breeding and isolation, for example, 1-2, HB92, and TS09-C strains. Some research groups attempted to transform heat-resistant strains into heat-resistant vectors, however, no successful research has been reported. For example, Jiang (Jiang, Yanlong, "Sequencing of whole genome of NDV V4 strain and the construction of cDNA clone," Northeast Agriculture University, doctoral dissertation, 2010) reported the construction of a transcription plasmid and a helper plasmid of a heat-resistant V4 strain, but fails to rescue a recombinant heat-resistant V4 strain. Further, Jiang (Jiang et al., "Plasmids driven minigenome rescue system for Newcastle disease virus V4 strain," Mol Biol Rep, 2009, Vol. 36(7), pp. 1909-1914) discloses the construction of a transcription plasmid and a helper plasmid of minigenomes of a heat-resistant V4 strain, which implements expression of an exogenous gene in cells, but a recombinant heat-resistant virus still could not be obtained.

Among numerous references about ND live vaccines, no ND live vaccine vector having a heat-resistant characteristic is reported. For example, Chinese Patent Application No. 200510097997.8, entitled "Newcastle Disease LaSota Vaccine Strain Reverse Genetic Manipulation System and Use Thereof," discloses a non-heat-resistant live vaccine vector based on an NDV LaSota vaccine strain, but the application does not concern a heat-resistant live vaccine vector. Chinese Patent Application No. 200610075781.6, entitled "Recombinant Attenuated Newcastle Disease LaSota Vaccine Strain Expressing HA Protein of Avian Influenza Virus H5 Subtype," discloses an avian influenza-ND bivalent genetic engineering live vaccine constructed by using an ND LaSota vaccine strain vector, but the application does not concern heat-resistant live vaccine vector.

Therefore, a heretofore unaddressed need exists in the art to address the aforementioned deficiencies and inadequacies.

SUMMARY OF THE INVENTION

In one aspect, the present invention is directed to an NDV live vaccine vector system having a heat-resistant feature.

In one embodiment, the heat-resistant NDV live vaccine vector system includes:

a) A transcription plasmid that has a complete genomic cDNA sequence of a heat-resistant NDV strain. The transcription vector is constructed by cloning the complete genomic cDNA sequence of a heat-resistant NDV vaccine strain to a pBR322 vector.

b) Three helper plasmids that are capable of respectively expressing NP, phosphoprotein, and large polymerase protein of a heat-resistant NDV strain. The three helper plasmids are constructed by respectively cloning genes of the NP, the phosphoprotein, and the large polymerase protein of a heat-resistant NDV vaccine strain to pcDNA3.1 vectors.

c) Host cells that allow replication of a heat-resistant NDV strain. The host cells are preferably BHK-21 cells.

In one embodiment, the heat-resistant NDV strain is a heat-resistant vaccine strain and specifically is a heat-resistant NDV vaccine strain TS09-C. The heat-resistant NDV vaccine strain TS09-C was deposited with China Center for Type Culture Collection (CCTCC) on May 9, 2011 under the accession number V201113.

In one embodiment, the host cells are BHK-21 cells.

In one embodiment, the genomic cDNA sequence of a heat-resistant NDV strain in the transcription plasmid is positioned after a T7 promoter and before a sequence coding a self-cleaving hepatitis D ribozyme and a T7 terminator.

In one embodiment, transcription plasmid has a DNA sequence of SEQ ID NO: 1.

In one embodiment, the transcription plasmid is inserted with and expresses an exogenous gene. In one embodiment, the inserting site of the exogenous gene in the transcription plasmid locates between a phosphoprotein gene and a matrix protein gene.

In one embodiment, the exogenous gene includes a marker gene or a virus antigen gene.

In one embodiment, the marker gene is a green fluorescent protein (GFP) gene.

In another aspect, the present application is directed to a method for using the heat-resistant live vaccine vector system to artificially obtain a recombinant heat-resistant NDV strain.

In one embodiment, the method includes the following steps.

1) Cotransfecting host cells, which allows replication of a heat-resistant NDV strain, with the transcription plasmid and the helper plasmids in the heat-resistant live vaccine vector system, and culturing the cotransfected host cells; and 2) harvesting the cell culture, and performing subculturing on host cells or specific pathogen free (SPF) chick embryos after the cell culture is filtered, thereby obtaining a recombinant heat-resistant NDV strain.

In one embodiment, the cotransfection in Step 1) is performed by calcium phosphate cotransfection.

In one embodiment, after the recombinant heat-resistant NDV strain is subjected to heat treatment at a temperature of 56° C. for one hour, hemagglutinin activity (HA) of the heat-resistant strain does not decline significantly. That is, the HA of the heat resistant strain is substantially the same before and after the heat treatment.

In one embodiment, the heat-resistant vaccine strain TS09-C is obtained with reference to Chinese Patent No. 201110163109.3, which is incorporated herein in its entirety.

In certain embodiments, the technical principle of the present invention is as follows. The transcription plasmid includes the complete genomic sequence of the heat-resistant NDV strain, and the three helper plasmids are capable of respectively expressing the NP, the phosphoprotein, and the large polymerase protein of the heat-resistant NDV strain. The host cells are preliminarily infected with a vaccinia virus capable of expressing T7 RNA polymerase, and then the cells are cotransfected with the transcription plasmid and the three helper plasmids. First, the vaccinia virus can express T7 RNA polymerase in the host cells. Next, the T7 RNA polymerase identifies a T7 promoter sequence on the transcription plasmid, starts a replication process of RNA, and terminates the replication at the T7 terminator. The RNA sequence obtained through the replication is a whole genomic RNA sequence of the heat-resistant NDV strain. The virus genomic RNA and the NP, the phosphoprotein, and the large polymerase protein expressed by the three helper plasmids form a nucleoprotein complex, and a first round of transcription of the virus RNA and translation and synthesis of virus protein are started. Components of the virus produce infectious progeny viruses through self-assembly. If exogenous genes, for example, GFP, are inserted into the transcription plasmid, the exogenous genes are replicated, transcribed, and expressed along with the ND whole genome sequence in the transcription plasmid and are assembled into a virion. Along with release, re-infection and proliferation of the virion, the exogenous genes are massively replicated and expressed in the host cells. In certain embodiments, the more efficient calcium phosphate cotransfection is adopted and the efficiency of cotransfecting the cells with the plasmids is improved. In certain embodiments, a sequence of the helper plasmid expressing an NP gene is modified, which improves expression efficiency of the NP gene in the cells. In addition, based on the newly bred heat-resistant strain TS09-C that is capable of proliferating efficiently on the BHK-21 cells, the possibility of successfully rescuing the virus is increased.

The present invention, among other things, has the following beneficial advantages.

1) In certain embodiments of the present application, based on the heat-resistant NDV vaccine strain, that is, the TS09-C strain (disclosed by the applicant in Chinese Patent Application No. 201110163109.3), the transcription plasmid and the helper plasmids of the TS09-C strain are constructed, a heat-resistant NDV live vaccine vector system is successfully constructed, and a recombinant virus having a heat-resistant characteristic is successfully obtained. Results of heat-resistant tests show that the heat-resistant characteristic of the recombinant heat-resistant virus is obviously higher than that of the TS09-C parent strain. In certain embodiments, a transcription plasmid inserted with a GFP gene is also constructed, and a heat-resistant NDV virus strain capable of expressing GFP and having a heat-resistant feature is also successfully rescued, which testifies an exogenous gene expression capability of the vector system. By utilizing the heat-resistant NDV live vaccine vector system established in certain embodiments of the present invention, recombinant heat-resistant ND live vaccines capable of expressing main antigen genes of other pathogens can be constructed.

2) Compared with related ND vaccines, the vaccines of the present invention has the following advantages: a) capability of simultaneously preventing two diseases; b) capability of being preserved at a temperature of 4° C. or even at room temperature, which greatly reduces the transportation cost; c) a high group infection rate; and d) convenient usage, the vaccine can be used in manners of food mixing, spraying, eye dropping, and nasal inhalation for immunization.

BRIEF DESCRIPTION OF THE DRAWINGS

The accompanying drawings illustrate one or more embodiments of the invention and together with the written description, serve to explain the principles of the invention. Wherever possible, the same reference numbers are used throughout the drawings to refer to the same or like elements of an embodiment, and wherein:

FIG. 3A and FIG. 3B show results of an indirect immunofluorescence assay of a recombinant heat-resistant NDV strain according to one embodiment of the present invention, in which FIG. 3A represents a test result of cells with recombinant viruses and FIG. 3B represents a test result of control cells;

DETAILED DESCRIPTION OF THE INVENTION

Figure 1:
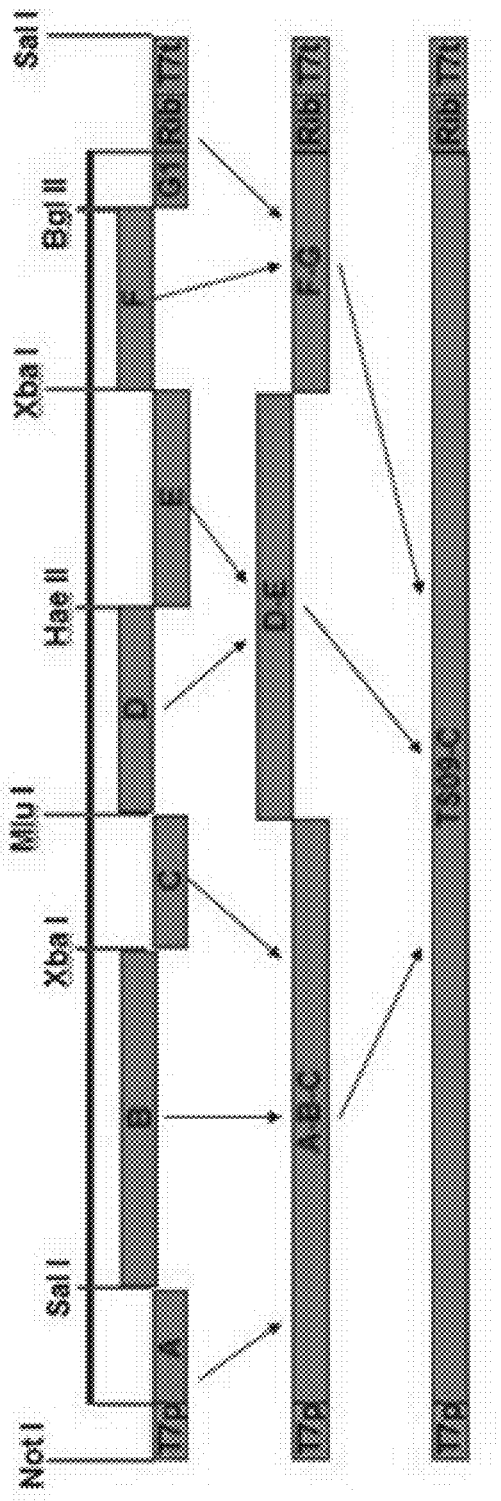
FIG. 1 is a schematic construction diagram of a transcription plasmid in a heat-resistant ND live vaccine vector system according to one embodiment of the present invention.
Figure 2:
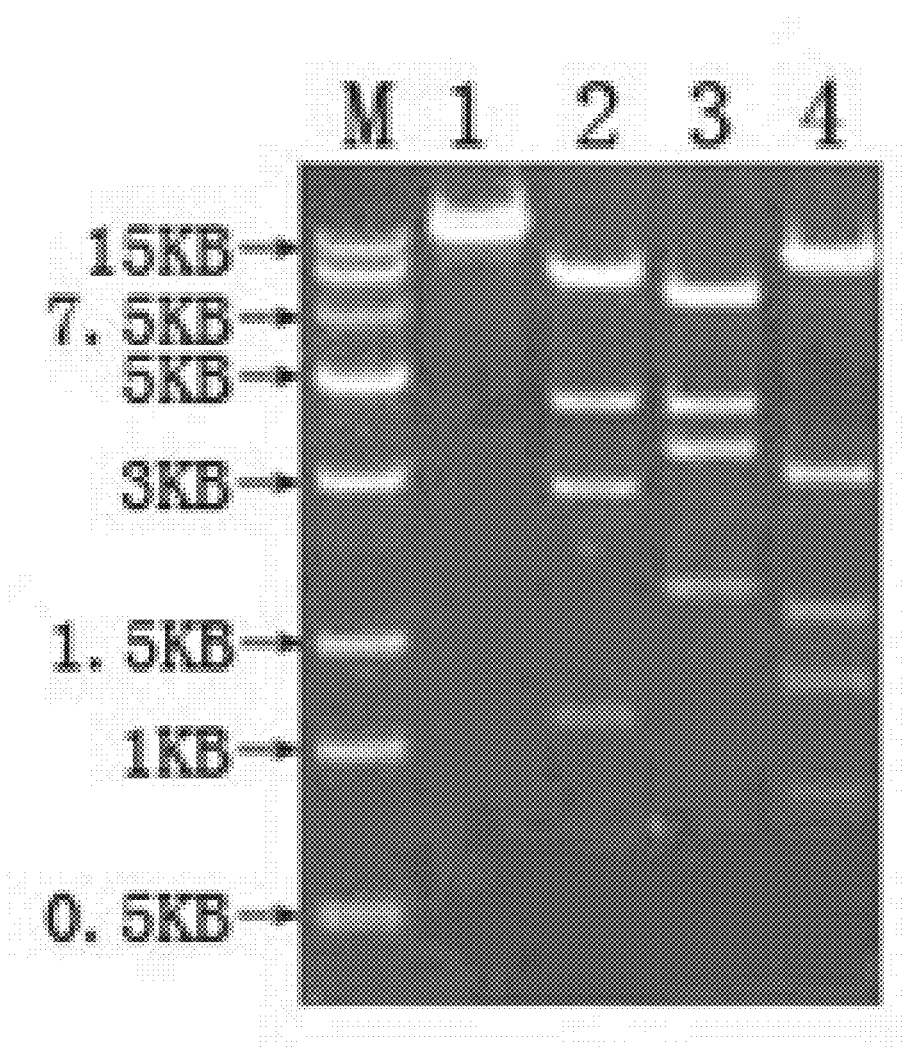
FIG. 2 is an enzyme digestion identification diagram of a transcription plasmid in a heat-resistant ND live vaccine vector system according to one embodiment of the present invention, in which M represents a DNA molecular weight standard, and 1, 2, 3, and 4 respectively represent enzyme digestion identification results of the transcription plasmid by NotI, BamHI, XhoI, and EcoRI.

The present invention is more particularly described in the following examples that are intended as illustrative only since numerous modifications and variations therein will be apparent to those skilled in the art. Various embodiments of the invention are now described in detail. Referring to the drawings, like numbers indicate like components throughout the views. As used in the description herein and throughout the claims that follow, the meaning of "a", "an", and "the" includes plural reference unless the context clearly dictates otherwise. Also, as used in the description herein and throughout the claims that follow, the meaning of "in" includes "in" and "on" unless the context clearly dictates otherwise. Moreover, titles or subtitles may be used in the specification for the convenience of a reader, which shall have no influence on the scope of the present invention.

As used herein, "around", "about", "substantially" or "approximately" shall generally mean within 20 percent, preferably within 10 percent, and more preferably within 5 percent of a given value or range. Numerical quantities given herein are approximate, meaning that the term "around", "about", "substantially" or "approximately" can be inferred if not expressly stated.

The present invention is further illustrated with reference to the accompanying drawings and embodiments, but content of the present invention is not limited to the following embodiments.

Embodiment 1: Construction of a Heat-Resistant NDV Live Vaccine Vector System

A heat-resistant NDV live vaccine vector system is formed by a transcription plasmid capable of expressing a complete genomic sequence of a heat-resistant NDV strain, three helper plasmids capable of expressing NP, phosphoprotein, and large polymerase protein of a heat-resistant NDV strain, and host cells. Construction of the transcription plasmid and the three helper plasmids are described below.

1. Construction of the Transcription Plasmid

A construction strategy of the transcription plasmid is shown in FIG. 1. The top black bar shows the full length genome of TS09-C strain. Each block shows a PCR or cloning segments. The whole genome is separated into 7 segments from A to G. First, a whole genome sequence is amplified through the 7 segments. Of them, a T7 promoter (T7p) sequence is added to the upstream of the segment A, and a hepatitis D virus ribozyme sequence (Rib) and a T7 terminator (T7t) sequence are added to the downstream of the segment G. Next, after the seven segments are obtained by performing amplification through conventional polymerase chain reaction (PCR), integrated PCR, and a primer self-extension, three intermediate plasmids pBR-ABC, pBR-DE, and pBR-FG are constructed. Then, a segment ABC and a segment DE from the corresponding plasmids are cut off and inserted into the front of a segment FG in the pBR-FG plasmid to form the transcription plasmid.

1.1 Extraction of Virus RNA and Reverse Transcription (RT) Reaction

Virus RNA purification kit, random primer, reverse transcriptase (including 5× RT buffer), dNTPs are purchased from Tiangen Biotech (Beijing) Co., Ltd. Genomic RNA of an NDV strain TS09-C is extracted according to the instruction of the RNA purification kit. The extracted RNA is dissolved in 50 µl diethypyrocarbonate (DEPC) water. A mixture is formed by adding 1 µl random primer into 17 µl of the above RNA solution (contains about 100 µg RNA). The mixture is kept at a temperature of 75° C. for 5 min, then immediately ice bathed. After that, an RT reaction solution including 5 µl 5× RT Buffer, 1 µl dNTPs (10 mmol/L), and 1 µl M-MLV reverse transcriptase is added. After being kept at a temperature of 42° C. for 60 min and being kept at a temperature of 95° C. for 5 min, the solution is preserved at a temperature of −20° C. for PCR reaction.

1.2 PCR Amplification and Clone of the Seven Segments

A PCR reaction system includes 10× Buffer, $MgCl_2$ (25 mmol/L), dNTPs, upstream and downstream primers (10 μmol/L), Taq enzyme, RT products, and water. Different upstream and downstream primers are used for amplification of different segments. Specific primer sequences are shown in Table 1 and listed as Sequence ID. NOs. 5-22, respectively. "-F" represents forward (upstream) primer and "-R" represents reverse (downstream) primer. For example, B-F and B-R are upstream primer (forward primer) and downstream primer (reverse primer) respectively and are used for amplifying B segment, C-F and C-R are upstream primer and downstream primer respectively and are used for amplifying C segment, and so on. Further, A-F and A-R are designed so that a T7 promoter sequence is added in the upstream of A segment. Furthermore, G1-F and G-R are primers for the G segment, G2-F and G2R are primers for G2 segment (include part of NDV sequence, Rib, and T7 terminator sequences), and G2-F2 and G2-R2 are primers for combining G1 and G2 together through fusion PCR.

PCR thermal cycle conditions are:

95° C. for 5 min;

30 cycles: 94° C. for 30 seconds, 55° C. for 2 min, and 72° C. for 5 min; and

72° C. for 10 min.

Each target band is detected through agarose gel electrophoresis. The specific positive band is purified and recovered through a DNA purification kit. The purified DNA is double digested by two corresponding restriction enzymes, and linked to a correspondingly digested clone vector. The ligated clone vector is then used to transform DH5α competent cell, and colonies are selected for PCR and enzyme digestion identification.

TABLE 1

Primers used for constructing the transcription plasmid (SEQ ID NOs. 5-22)

| Primer | Sequence |
|---|---|
| A-F | CCGGGCGGCCGCGTAATACGACTCACTATAGGACCAAACAG AGAATCTGTGAGTTACG |
| A-R | CTGTGATATCGCCTCCATCATAGAC |
| B-F | CAGAGCAGAGCCAAGACAATACTCC |
| B-R | CCTATCTACTACATCTTGATTGGAACCG |
| C-F | CGGCGAATTCGCATCATCGAGCGCCCGCTATAGCATGGAGG CCAGCACACC |
| C-R | CGGAAGCTTAGATAAGACGGCCTGCTGTACGC |
| D-F | CGCGGATCCGATACAATGACACATGTCCAGATGAGC |
| D-R | GCAGGTTGAATGCGAAGAAATCC |
| E-F | GGGTAATCAAGTCTACGATGTTGTAGC |
| E-R | GGCGAAGCTTAAGAATGTTCATTAGCTCGATTGTGG |
| F-F | GGTGACTTTGCGAGACTTGACTTAGC |
| F-R | CCAATATTGTGACCTCTAAGATCTGCC |
| G1-F | AGAGAACATCACTTAAACAGTGCACAAGG |
| G1-R | CCATGCCGACCCACCAAACAAAGATTTGGTGAATGAC |

TABLE 1 -continued

Primers used for constructing the transcription plasmid (SEQ ID NOs. 5-22)

| Primer | Sequence |
|---|---|
| G2-F | TTCACCAAATCTTTGTTTGGTGGGTCGGCATGGCATCTCCA CCTCCTCGCGGTCCGACCTGGGCATCCGAAGGAGGACGCAC GTCCACTCGGATGGCTAAGGGAGGGGCACTCCGCGGTCACT GCTAACAAAGC |
| G2-R | CCTGACGTCGACAGCTCCAGCAAAAAACCCCTCAAGACCCG TTTAGAGGCCCCAAGGGGTTATGCTAGTTATTGCTCAGCGG TGGCAGCAGCCAACTCAGCTTCCTTTCGGGCTTTGTTAGCA GTGACCGCGGAGTGC |
| G2-F2 | TTCACCAAATCTTTGTTTGGTGGG |
| G2-R2 | CCTGACGTCGACAGCTCCAGC |

1.3 Ligation of the Segments to Form the Transcription Plasmid and Identification of the Transcription Plasmid As shown in FIG. 1, seven clone plasmids are identified and digested with corresponding restriction enzymes to form 7 segments, i.e., A (including T7p), B-F and G (including Rib and T7t). A pBR322 plasmid is digested with Not I and Mlu I and ligated with segments A, B and C to form the pBR-ABC plasmid. A pBR322 plasmid is digested with Mlu I and Xba I and ligated with segments D and E to form the pBR-DE plasmid. A pBR322 plasmid is digested with Xba I and Sal I and ligated with segments F and G to form the pBR-FG plasmid. In certain embodiments, the enzyme digestion conditions are: mixing 2 μl 10× buffer, 1 μg plasmid, 1 μl restriction enzyme, and adding water to a total volume of 20 μl, and incubating at 37° C. for 1 hour. In certain embodiments, the ligation conditions are: mixing 1 μl 10× buffer, 1 μg DNA fragments chosen from the 7 segments, 1 μg plasmid fragment, 1 μl ligase, and adding water to a total volume of 10 μl, and incubating at 16° C. for 12 hours. Subsequently, the three intermediate plasmids pBR-ABC, pBR-DE and pBR-FG are digested, to insert the fragments ABC and DE into the pBR-FG plasmid and form the transcription plasmid.

FIG. 2 shows an enzyme digestion result of the transcription plasmid. The constructed transcription plasmid is correct through enzyme digestion verification. Further, the transcription plasmid was sent to Shanghai Sangon Biological Engineering Technology & Services Co., Ltd for whole plasmid sequencing. The full length DNA sequence of the transcription plasmid is shown in SEQ ID NO: 1, with a length of 19178 bp. Comparing with the sequence of the TS09-C parent strain, the transcription plasmid with SEQ ID NO: 1 contains six random mutations.

2. Construction of the Helper Plasmids

PCR amplification is performed by using the transcription plasmid as a PCR template, to respectively obtain three genome segments encoding NP, phosphoprotein, and large polymerase protein. The three segments are respectively cloned to eukaryotic expression vectors by enzyme digestion and ligation. Plasmid extraction and enzyme digestion identification are performed on a bacterial culture with a positive PCR test result. A result thereof shows that the three constructed helper plasmids, that is, pcDNA-NP, pcDNA-P, and pcDNA-L, are all correct. The three helper plasmids identified to be correct are sent to Shanghai Sangon Biological Engineering Techonolgy & Services Co., Ltd for sequencing. A sequence of the helper plasmid pcDNA-NP is SEQ ID NO: 2, and a full length of the sequence is 6876 bp. A sequence of the helper plasmid pcDNA-P is SEQ ID NO: 3, and a full length of the sequence is 6597 bp. A sequence of the helper plasmid pcDNA-L is SEQ ID NO: 4, and a full length of the sequence is 12041 bp. To improve expression efficacy of the helper plasmids in cells, a starting sequence of an NP gene can be modified. In certain embodiments, Kozak sequence (GC-CACCATGG, the underlined sequence is the starting sequence of the gene) is added to NP, P and L gene. For P and L genes, the starting sequence is the same as the Kozak sequence, i.e., ATGG. However, for NP gene, the starting sequence is ATGT instead of ATGG. That is, in order to improve the expression of the NP helper plasmids, the fourth nucleic acid was changed from T to G.

Embodiment 2: Obtaining a Recombinant Heat-Resistant NDV Strain Using a Heat-Resistant NDV Live Vaccine Vector System A transcription plasmid and helper plasmids in a heat-resistant NDV live vaccine vector system are used to cotransfect host cells allowing replication of a heat-resistant NDV strain. The cotransfected host cells are cultured and the cell culture is collected, and used for sub-culture on the host cells or SPF chick embryos for proliferation, thereby obtaining a recombinant heat-resistant NDV strain.

1. Artificially Rescuing a Recombinant Heat-Resistant NDV Strain

BHK-21 cells are adjusted to an optimal state, and seeded to a 6-well plate (cell density of $4 \times 10^5$ cells/ml). The cells grow to 80-90% confluence after sub-culturing for one day. The cell nutrient solution is changed into a Dulbecco's modified Eagle medium (DMEM) culture medium with 2% new-born calf serum. The BHK-21 cells are infected with a vaccinia virus vTF7-3 at a multiplicity of infection (MOI) of 0.01 for one hour. After that, according to the instruction and using calcium phosphate transfection kit from Invitrogen, the transcription plasmid and the three helper plasmids are used to cotransfect the BHK-21 cells by calcium phosphate method. The amounts of the plasmids used for cotransfection are respectively 2 μg, 0.5 μg, 0.5 μg, and 1 μg. After six hours from the cotransfection (or before the cells overgrow), the cell culture medium is changed into a DMEM culture medium that does not contain new-born calf serum, and tosyl-phenylalanine chloromethyl-ketone (TPCK) treated trypsin is added thereto. After obvious pathological changes occur to the cells, the cells are frozen and thawed twice. A supernatant is harvested. Vaccinia viruses are filtered out through a 0.22 μm filter membrane, and then subcultured for three continuous passages on the SPF chick embryos.

2. Indirect Immunofluorescence Assay of the Recombinant Virus

Figure 3A:
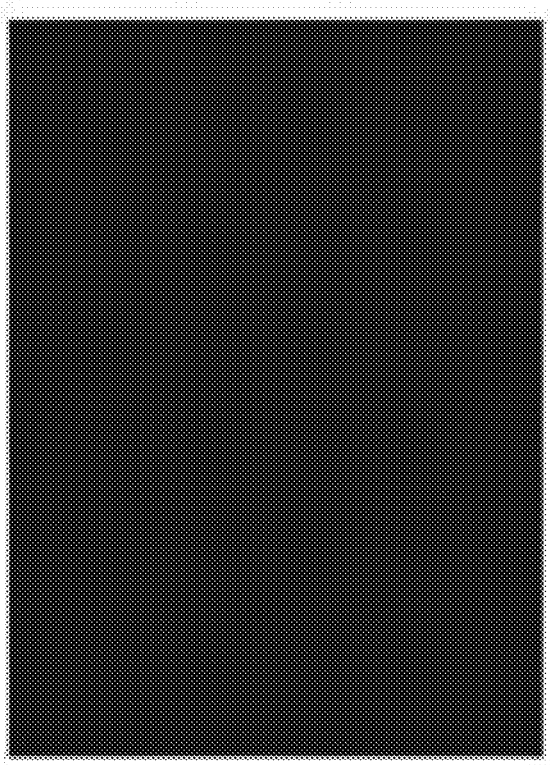
Figure 3B:
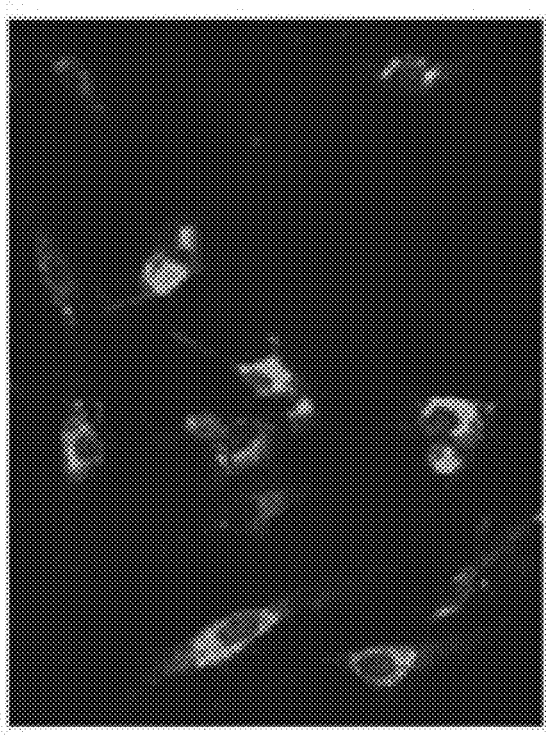

BHK-21 cells are seeded to a 6-well plate. When the cells grow to 80-90% confluence, the cells are washed three times using Hank's solution, and then 0.5 ml recombinant virus solution to be tested is added to the cells. After culturing at a temperature of 37° C. for one hour, the culture medium is changed to a DMEM culture medium that does not contain new-born calf serum, and TPCK treated trypsin (0.2 μg/mL) is added. After culturing at 37° C. for about 72 hours, an indirect immunofluorescence assay can be performed. The culture medium is aspirated, and the cells are rapidly washed three times using phosphate buffer solution (PBS). The cells are fixed using acetone:ethanol (1:1) and are placed at −20° C. for 20 min. Then the fixative solution is aspirated. The cells are rinsed three times using PBS, and a NDV polyclonal antibody working solution is added at 100 μl/well to the rinsed cells. After incubation at a temperature of 37° C. for one hour, the polyclonal antibody working solution is aspirated. After the cells are rinsed three times using PBS, a working solution of a fluorescein isothiocyanate (FITC) labeled secondary antibody is added thereto at 100 μl/well. After incubation at 37° C. for one hour, the secondary antibody working solution is aspirated. The cells are rinsed three times using PBS, and a small amount of PBS is left in the well. The plate is placed under an inverted fluorescence microscope for observation, recording and photographing. The results of the indirect immunofluorescence assay are shown in FIGS. 3A and 3B. FIG. 3A shows the cells transfected by the recombinant virus, in which fluorescent signals are observed after immunofluorescent staining. FIG. 3B shows the cells not transfected by the recombinant virus, in which no fluorescent signals are observed after immunofluorescent staining.

3. Transmission Electron Microscopy of the Recombinant Virus

Figure 4:
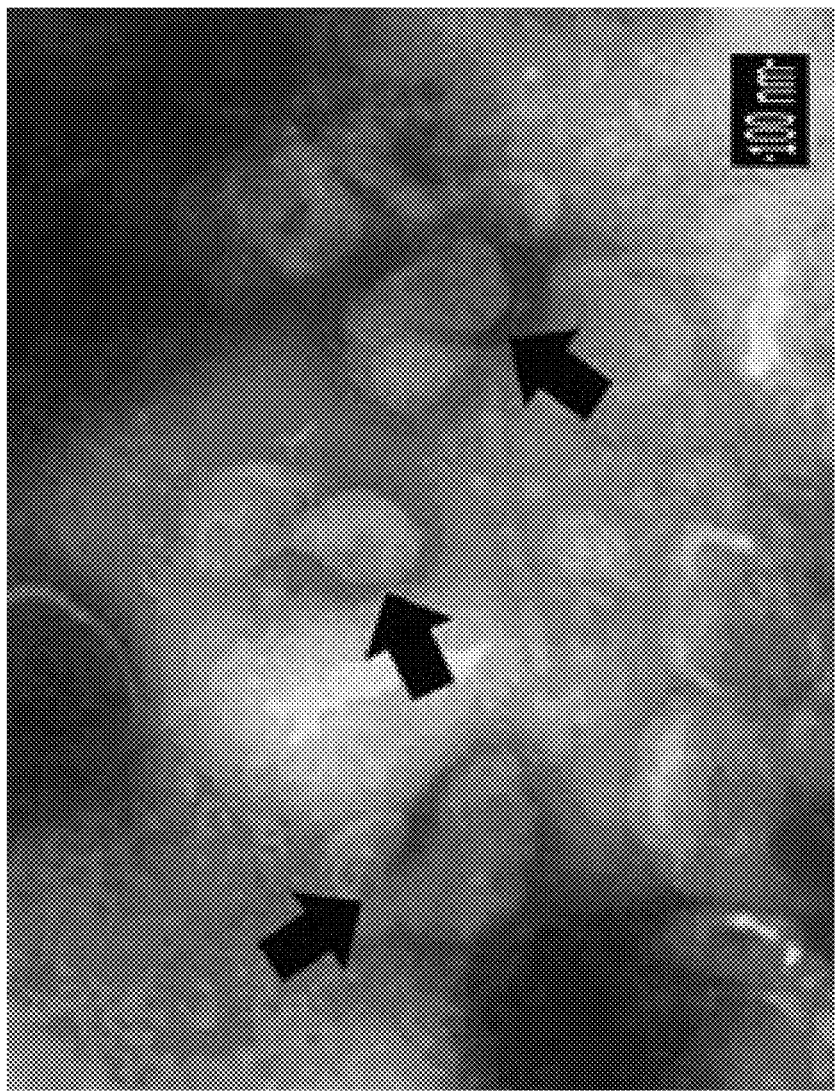
FIG. 4 shows a transmission electron microscopy of a recombinant heat-resistant NDV strain according to one embodiment of the present invention, in which typical NDV particles are marked by arrows.

An SPF chick embryo is inoculated with the recombinant virus solution, and cultured for 120 hours. Allantoic fluid of the chick embryo is harvested. The harvested allantoic fluid is separated, purified and condensed through sucrose gradient centrifugation and ultracentrifugation. The processed sample is negatively stained and observed using an electron microscope. The electron micrograph image is shown in FIG. 4. Virions having a capsule membrane are observed, which is a proof that the recombinant NDV is successfully rescued.

Embodiment 3: Biological Characteristics of the Recombinant Heat-Resistant NDV Strain After the recombinant heat-resistant NDV strain is artificially obtained, biological characteristics of the recombinant virus is tested to determine whether the recombinant heat-resistant NDV strain has the same biological characteristics as the TS09-C parent strain.

1. Cell Growth Curve of the Recombinant Heat-Resistant NDV Strain

Figure 5:
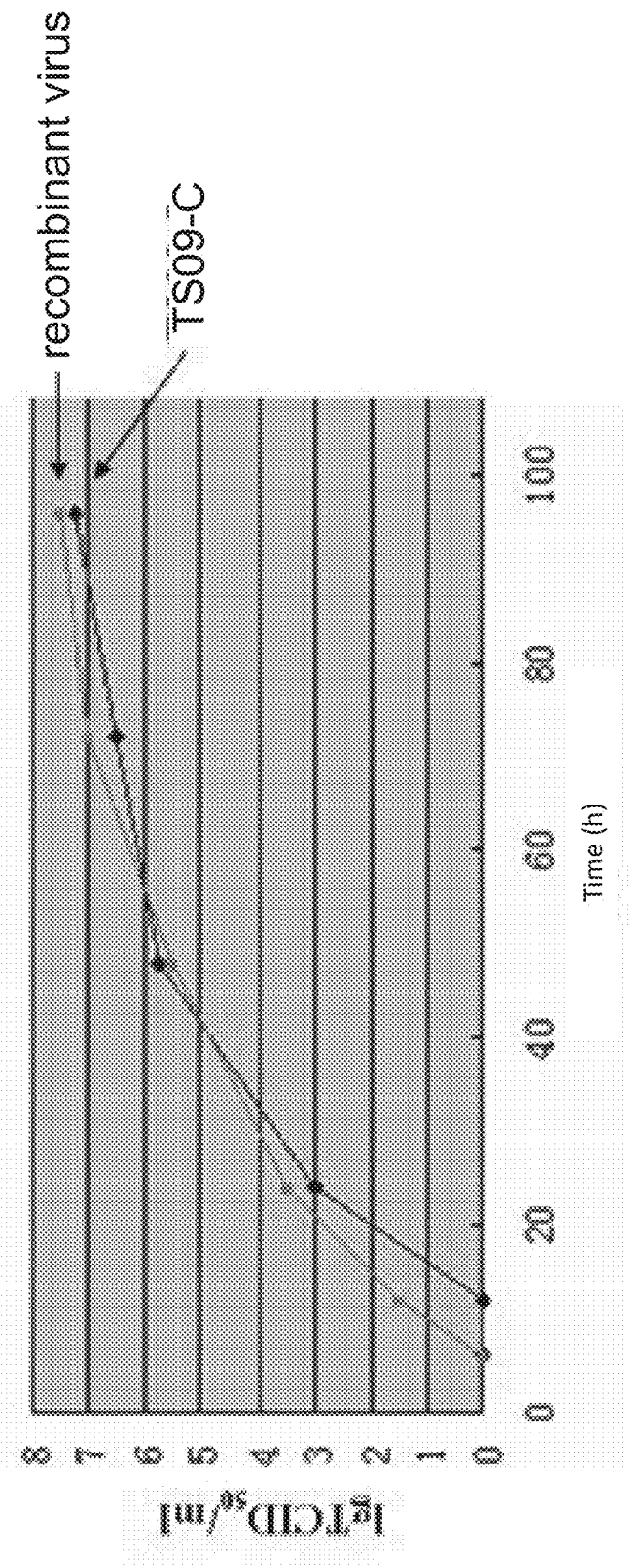
FIG. 5 is a growth curve of a recombinant heat-resistant NDV strain according to one embodiment of the present invention comparing with that of the TS09-C strain. in which a vertical coordinate represents a virus titer with 1 gTCID$_{50}$/ml as the unit, and a horizontal coordinate represents a culturing time with hour as the unit.

A diluted virus solution is used to inoculate BHK-21 cells that have grown into a compact monolayer. Supernatants of the cell culture are collected at 6 hours, 12 hours, 24 hours, 48 hours, 72 hours, and 96 hours after the infection, and the virus titer are measured. In one example, a method includes the following steps. The virus solution is 10-fold serial diluted in the range of about $10^{-1}$ to $10^{-8}$. 100 μl of the solution at each dilution is added to a 96-well plate containing the monolayer of BHK-21 cells. Each dilution includes 5 repeats. After one hour of infection, removing the culture medium and adding a DMEM medium containing 5% serum. The cells are cultured at 37° C., and then observed for pathological changes. $TCID_{50}$ is calculated based on the number of wells with pathological cells. According to the measured virus titer and a corresponding culture time point, a cell growth curve of the recombinant heat-resistant NDV strain is obtained. As shown in FIG. 5, the recombinant virus has a highest proliferation titer in 96 hours after the infection, which is $10^{7.0} TCID_{50}$/ml, and has a proliferation titer similar to that of the TS09-C parent strain.

2. Safety Test of the Recombinant Virus in Chicken

Safety of the recombinant virus in chicken is assessed by measuring a mean death time (MDT) and an intracerebral pathogenicity index (ICPC) of chick embryos. The MDT method is as follows. A virus solution is 10-fold diluted using a physiological saline solution. The diluted solution is inoculated to SPF chick embryos at the age of nine days with an inoculation amount of 0.1 ml/embryo. Eggs are candled twice each day and are observed for seven consecutive days. Death time of chick embryos is recorded, and a MDT value is calculated. The ICPI measurement method is as follows. The 10-fold diluted virus solution is inoculated, with an inoculation amount of 0.05 ml/chick and in an intracerebral manner, to 10 SPF chicks that are 24 to 40 hours after hatching. The chicks are observed once a day and are graded. A normal chick is graded 0, a diseased chick is graded 1, and a dead chick is graded 2. The chicks are observed for 8 days, and an ICPC value is calculated. A result thereof shows that the MDT value of the recombinant virus is greater than 150 hours, and the ICPI value thereof is 0.00. Therefore, the recombinant virus maintains a characteristic of being non-toxic and safe to chicks of the TS09-C parent strain.

3. Heat-Resistant Characteristic Test of the Recombinant Virus

The recombinant virus is placed in a water bath at a temperature of 56° C. for heat treatment. The virus solutions are respectively collected at 6 minutes, 15 minutes, 30 minutes, 60 minutes, 90 minutes, 120 minutes, and 150 minutes and used for measuring HA activity and infectivity in chick embryos. As shown in Table 2, HA activity of the recombinant virus has a heat-resistance of about 120 minutes, and infectivity of the recombinant virus has a heat-resistance of about 120 minutes. In comparison, HA activity of the TS09-C parent strain has a heat resistance of about 60 minutes, and infectivity of the TS09-C parent strain has a heat-resistance of about 60 minutes. Further, HA activity of the control LaSota strain has a heat-resistance of about 6 minutes.

In certain embodiments, mutations in the transcription vector contribute to the heat-resistance of recombinant viruses. In this example, comparing the genomic sequence of the recombinant virus and the TS09-C strain, mutations in the recombinant virus, $A_{6801}T$, $G_{7528}A$, $T_{7734}A$, $A_{10340}G$, $A_{12607}G$ and $A_{12991}G$ are present. The mutations can contribute to the improved heat-resistance of the recombinant virus.

TABLE 2

Heat-resistance test of the recombinant virus

| Measurement item | Virus strain | Heat treatment time (minute) | | | | | | |
|---|---|---|---|---|---|---|---|---|
| | | 6 | 15 | 30 | 60 | 90 | 120 | 150 |
| HA activity | Recombinant virus | + | + | + | + | + | + | − |
| | TS09-C strain | + | + | + | + | − | − | − |
| | LaSota strain | + | − | − | − | − | − | − |
| Infectivity in chick embryos | Recombinant virus | + | + | + | + | + | + | − |
| | TS09-C strain | + | + | + | + | − | − | − |

Figure 6:
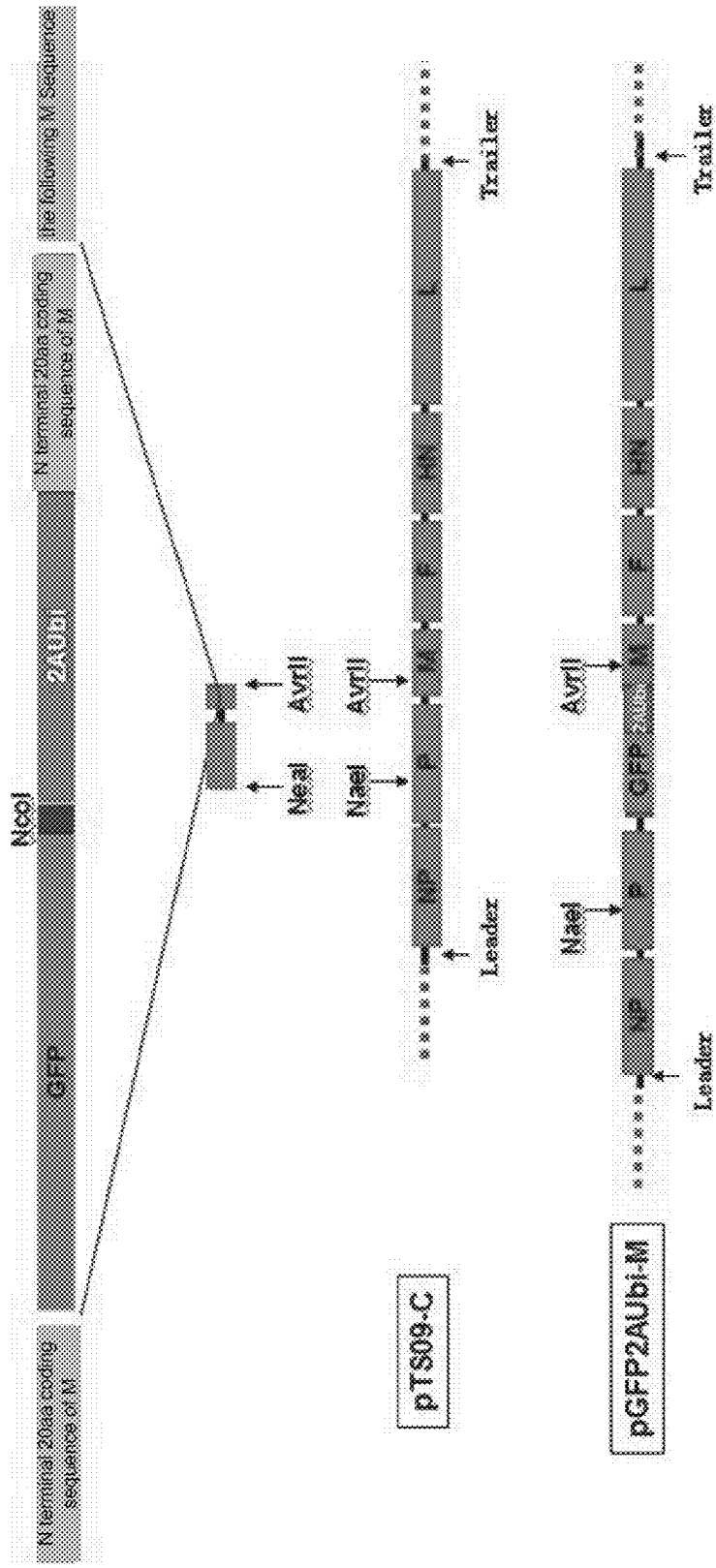
FIG. 6 is a schematic construction diagram of a transcription plasmid inserted with a GFP gene according to one embodiment of the present invention, in which pGFP2AUBI-M represents a transcription plasmid inserted with a GFP gene, and pTS09-C represents a transcription plasmid without inserted exogenous gene.

Embodiment 4: Expression of a GFP Gene in a Heat-Resistant NDV Live Vaccine Vector 1. Construction of a Transcription Plasmid Inserted with a GFP Gene According to the protocol shown in FIG. 6, a GFP gene is inserted into a transcription plasmid of a heat-resistant NDV live vaccine vector system by enzyme digestion and ligation. The insertion position of the GFP gene is between a P gene and an M gene of the transcription plasmid. Enzyme digestion and sequencing identification are performed on the transcription plasmid inserted with the GFP gene, and the results confirm the correct insertion of the GFP gene. It is indicated that a transcription plasmid inserted with a GFP gene is successfully constructed.

Figure 7B:
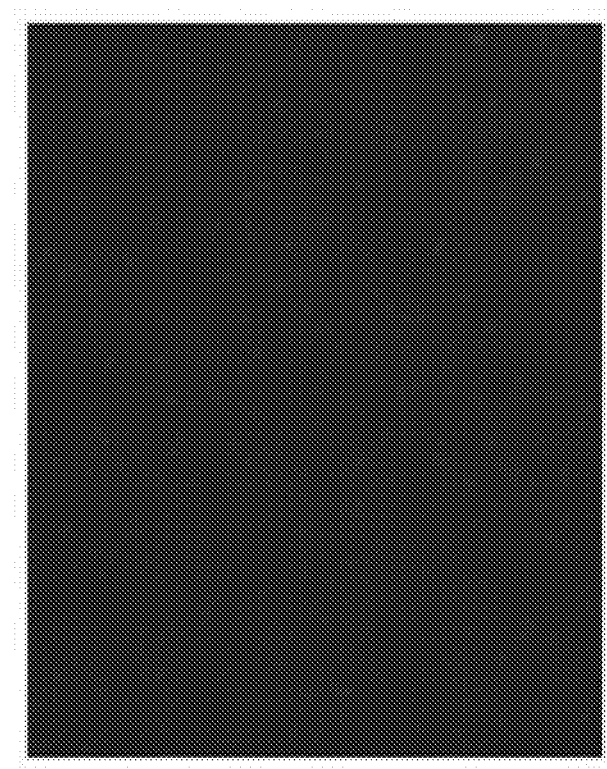
FIG. 7B is a fluorescent image of a control BHK-21 cells.
Figure 7A:
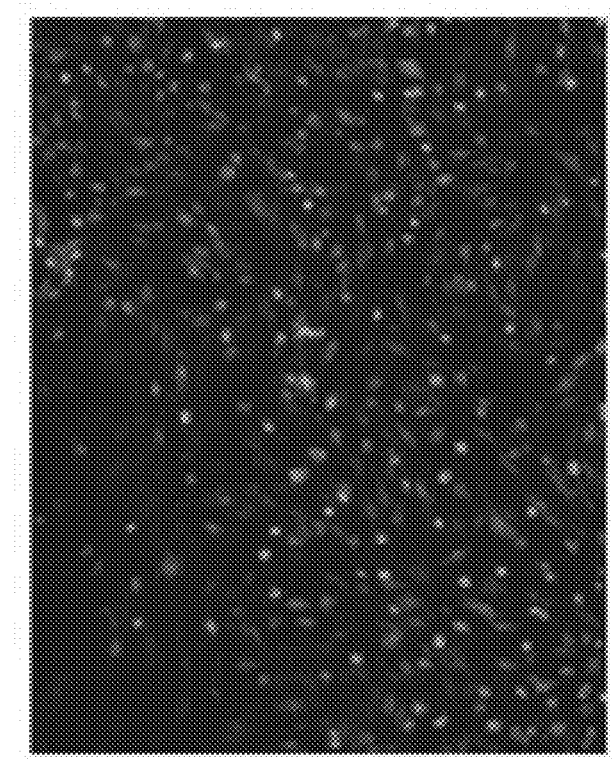
FIG. 7A is a fluorescent image showing that a recombinant heat-resistant NDV strain according to one embodiment of the present invention expresses GFP protein in BHK-21 cells.

2. Artificially Rescuing a Recombinant Heat-Resistant NDV Strain Expressing GFP Protein The transcription plasmid inserted with a GFP gene and three helper plasmids are used to cotransfect BHK-21 cells by a liposome (Lipo2000) method. The amounts of the plasmids used for cotransfection are 2 µg, 0.5 µg, 0.5 µg, and 1 µg respectively. At six hours after the cotransfection (or before the cells overgrow), the cell culture medium is changed into a DMEM culture medium that does not contain newborn calf serum, and TPCK treated trypsin is added. Generation of green fluorescent signals and status of the cells are observed each day through an inverted fluorescence microscope. After obvious pathological changes occur to the cells, the cells are frozen and thawed twice. A supernatant is harvested, and vaccinia viruses are filtered out through a 0.22 µm filter membrane. Sub-culturing is directly performed on the cells, and generation of green fluorescent signals is observed and recorded. As shown in FIG. 7A, specific green fluorescent signals are observed in 24 hours after the BHK-21 cells are infected with the recombinant virus expressing GFP protein. In comparison, as shown in FIG. 7B, no fluorescent signals are found in control cells. Therefore, a recombinant heat-resistant NDV strain capable of expressing GFP protein is artificially rescued in this embodiment.

Compared with related art, a greatest characteristic of the present invention is that the artificially obtained recombinant NDV has a heat-resistant feature and it is also the first time that an NDV live vaccine vector system having a heat-resistant feature is established. The present invention has a great application prospect in aspects of research and development of mixed (polyvalent) heat-resistant genetic engineering live vaccines for major poultry diseases including ND and avian influenza and research on a heat-resistant mechanism of viruses.

The foregoing description of the exemplary embodiments of the invention has been presented only for the purposes of illustration and description and is not intended to be exhaustive or to limit the invention to the precise forms disclosed. Many modifications and variations are possible in light of the above teaching.

The embodiments are chosen and described in order to explain the principles of the invention and their practical application so as to activate others skilled in the art to utilize the invention and various embodiments and with various modifications as are suited to the particular use contemplated. Alternative embodiments will become apparent to those skilled in the art to which the present invention pertains without departing from its spirit and scope. Accordingly, the scope of the present invention is defined by the appended claims rather than the foregoing description and the exemplary embodiments described therein.

What is claimed is:

1. A heat-resistant Newcastle disease virus (NDV) live vaccine vector system, comprising:
 a transcription plasmid, comprising a complete genomic cDNA sequence of a heat-resistant NDV strain, and an exogenous gene inserted between the phosphoprotein gene and the matrix protein gene of the heat-resistant NDV;
 a first helper plasmid, comprising a DNA sequence encoding the nucleoprotein (NP) of the heat-resistant NDV strain;
 a second helper plasmid, comprising a DNA sequence encoding the large polymerase protein of the heat-resistant NDV strain;
 a third helper plasmid, comprising a DNA sequence encoding the large polymerase protein of the heat-resistant NDV strain; and
 host cells allowing replication of the heat-resistant NDV strain,
 wherein the transcription plasmid comprises the nucleotide sequence of SEQ ID NO: 1.

2. The heat-resistant NDV live vaccine vector system of claim 1, wherein the host cells are BHK-21 cells.

3. The heat-resistant NDV live vaccine vector system of claim 1, wherein the exogenous gene comprises at least one of a marker gene and a virus antigen gene.

4. The heat-resistant NDV live vaccine vector system of claim 3, wherein the marker gene is a green fluorescent protein (GFP) gene.

5. A heat-resistant Newcastle disease virus (NDV) live vaccine vector system, comprising:
 a transcription plasmid, comprising a complete genomic cDNA sequence of a heat-resistant NDV strain, and an exogenous gene inserted between the phosphoprotein gene and the matrix protein gene of the heat-resistant NDV;
 a first helper plasmid, comprising a DNA sequence encoding the nucleoprotein (NP) of the heat-resistant NDV strain;
 a second helper plasmid, comprising a DNA sequence encoding the large polymerase protein of the heat-resistant NDV strain;
 a third helper plasmid, comprising a DNA sequence encoding the large polymerase protein of the heat-resistant NDV strain; and
 host cells allowing replication of the heat-resistant NDV strain,
 wherein the first helper plasmid comprise the nucleotide sequence of SEQ ID NO: 2, the second helper plasmid comprise the nucleotide sequence of SEQ ID NO: 3, and the third helper plasmid comprise the nucleotide sequence of SEQ ID NO: 4.

6. The heat-resistant NDV live vaccine vector system of claim 5, wherein the host cells are BHK-21 cells.

7. The heat-resistant NDV live vaccine vector system of claim 5, wherein the complete genomic cDNA sequence of the heat-resistant NDV strain in the transcription plasmid is positioned after a T7 promoter and before a self-cleaving hepatitis D ribozyme coding sequence and a T7 terminator.

8. The heat-resistant NDV live vaccine vector system of claim 5, wherein the exogenous gene comprises at least one of a marker gene and a virus antigen gene.

9. The heat-resistant NDV live vaccine vector system of claim 5, wherein the marker gene is a green fluorescent protein (GFP) gene.

* * * * *

SEQUENCE LISTING

<160> NUMBER OF SEQ ID NOS: 22

<210> SEQ ID NO 1
<211> LENGTH: 19178
<212> TYPE: DNA
<213> ORGANISM: Artificial Sequence
<220> FEATURE:
<223> OTHER INFORMATION: Transcription Vector

<400> SEQUENCE: 1

```
cgatggcgcc agctgcaggc ggccgcgtaa tacgactcac tataggacca aacagagaat    60
ctgtgagtta cgatagaagg cgaaggagca atcgaagtcg tacgggtaga aggtgtgaat   120
ctcgagtgcg agcccgaagc tcaaactcga gagagccttc tgccaaaatg tcttctgtat   180
tcgatgagta cgagcagctc ctcgcggctc agactcgccc caatgagct catggcggag    240
gagagaaggg gagcacctta aaggtagaag tcccggtatt cactctcaac agtgatgacc   300
cagaagatag atggaactt tgcagtgttt tgtcttcggat tgctgttagc gaggatgcca   360
acaaaccact taggcaaggt gctctcatat ctctcttatg ttcccactct caagtgatga   420
ggaaccatgt tgcccttgcg gggaaacaga atgaggccac actggctgtt cttgagatcg   480
atggttttac caacggcgtg ccccagttca acaacaggag tggagtgtct aagagagag    540
cacagagatt tatgatgata gcagggtctc tccctcgggc atgcagcaac ggtaccccgt   600
tcgtcacagc tggggttgaa gatgatgcac cagaagacat tactgatacc ctggagagga   660
tcctctctat ccaggctcaa gtatgggtca cggtggcaaa ggccatgact gcatatgaga   720
cagcagatga gtcagaaaca agaagaatca ataagtacat gcagcaaggc agggtccaga   780
agaagtacat cctccacccc gtatgcagga gcgcaatcca actcacaatc agacagtctc   840
tggcggtccg catcttttttg gttagcgagc ttaagagagg ccgcaacacg gcaggtggga   900
cctccaccta ttacaacttg gtgggggatg tagactcata catcaggaac actgggctaa   960
ctgcattctt cctgacactt aaatatggaa ttaacaccaa gacatcagcc cttgcactta  1020
gcagcctctc aggcgatatc cagaaaatga agcagctcat gcgcttgtat cggatgaaag  1080
gagataatgc gccgtacatg acattgctcg gtgacagtga ccagatgagc tttgcacctg  1140
ccgagtatgc acaactttac tcctttgcca tgggtatggc atcagtccta gataaaggaa  1200
ctagcaaata ccaatttgcc agggacttta tgagcacatc attctggaga cttggagtag  1260
agtatgctca ggctcaagga agtagcatca atgaggatat ggccgccgag ctaaagctaa  1320
ccccagcagc aaggagaggc ctggcagctg ctgcccaaag agtgtctgag gagaccagca  1380
gcatggacat gcccacccaa caagccgggg tcctcactgg actcagcgac ggaggctccc  1440
aagcccccca aggtgcactg aacagatcac aagggcaacc ggacaccggg gacggggaga  1500
cccaatttct ggatctgatg agagcggtgg caaatagcat gagagaagcg ccaaactctg  1560
cgcagggcac ccctccaccg gggcctcccc caacccctgg gccctctcaa gacaatgaca  1620
ccgactgggg gtactgaccg acagcaccca gtttgcttct atgaggtcat cccaattcct  1680
ctgcccacac cccacccctc aatccgcaat cccgcatggc caaacccaca acgaacccc    1740
cctgtctccc tcctctcccc cagccccaca accccacctg cccagggcaa cataggtaca  1800
atgcgaccca ctaataatca atacagggcc aaagaaatta gaaaaagta cgggtagaag    1860
ggagacattc agagatcagg gcgagtcacc cgggtctctg ctctcccttc tacctagtgg   1920
attaggatgg agatggccac ctttacagat gcggagatcg acgagctatt tgagaccagt   1980
ggaactgtca ttgacagcat aattacggcc cagggaaaac cagtagagac tgttggaagg   2040
agtgcaatcc cacaaggcaa aactaaggct ttgagcgcag catgggagaa gcatgggagc   2100
atccagtcac cagccagcca agacacccct gatcgacagg acagatcaga taaacaactg   2160
tccacacccg agcaagcgag tccaaacgac agccccccag ccacatccac tgaccagcct   2220
cccactcagg ctgcagatga ggccggcgat acacagctca agaccggagc aagcaactct   2280
ctgctgtcga tgcttgataa actcagcaat aagtcatcta atgctaaaaa gggcccaggg   2340
```

```
tcgagccctc aagaaaggca tcatcaacgt ctgactcaac aacagggag tcaacaaagc    2400 cgcggaaaca gccaagagag accgcagaac caggccaagg ccatccctgg aaaccaggtc    2460
acagacgcga acacagcata tcatggacaa tgggaggagt cacaactatc agctggtgca    2520
acccatcatg ctctccgatc agagcagagc caagacaata ctcctgcacc tgtggatcat    2580
gtccagctac ctgtcgactt tgtgcaggcg atgatgtcta tgatggaggc gatatcacag    2640
agggtaagta aagttgacta tcagctggac cttgtcttga aacagacatc ttctatcccc    2700
atgatgcggt ctgaaatcca gcagctgaaa acgtctgttg cggtcatgga agccaatttg    2760
ggcatgatga agatcctgga ccctggttgt gccaacgttt catctctaag tgatctacgg    2820
gcagttgccc gatcccaccc ggttttaatt tctggccccg agacccatc tccttatgtg    2880 acccaagggg gcgaaatggc actcaataaa ctttcgcaac cggtgcaaca ccctctgaa    2940 ttgattaaac ccgccacggc aagcgggcct gatataggag tggagaaaga cactgtccgt    3000
gcattgatca tgtcacgccc tatgcatccg agctcttcag ctaggctctt gagcaaactg    3060
gacgcagccg gatcgattga ggaaatcaga aaaatcaagc gccttgcact gaatggctaa    3120
tcaccaccgc aacccgcagc agatccctgt ccacccagca ccacgggta tctgcaccaa    3180 gctcctctct gcaaacccaa ggtccaacac cccgagcgac aaccctgtcc tgcttcctct    3240
gccccactaa atgatcgcgc agctgcaatc aattcagcta tattaaggat taagaaaaaa    3300
tacgggtaga atcggagtgc cccgattgtg ccaagatgga ctcatctagg acaatcgggc    3360
tgtactttga ttctacccctt ccttctagca acctgctagc attcccgata gtcctacaag    3420
acacagggga cgggaagaag caactcgccc cgcaatacag gatccagcgt cttgactcgt    3480
ggacatacag caaagaagac tcggtattca tcaccaccta tggattcatc tttcaggttg    3540
ggaatgaaga agccactgtc ggcatgatca atgataatcc caagcgcgag ttactttcca    3600
ctgccatgct atgcctaggg agtgtaccaa atgtcggaga tcttgttgag ctggcaaggg    3660
cctgcctcac tatggtggta acatgcaaga agagtgcaac taacaccgag agaatagtct    3720
tctcagtagt gcaggcaccc caggtgctgc aaagctgtag ggttgtggca aacaaatact    3780
cgtcggtgaa tgcagtcaag cacgtgaaag caccagagaa gattcctggg agcggaaccc    3840
tagagtacaa agtgaacttt gtctctctga ccgtggtgcc aagaaaggac gtctacaaga    3900
taccaactgc agcacttaag gtctctggct caagtctgta caatcttgcg ctcaatgtca    3960
ctattgatgt ggaggtagac ccgaagagcc cgttggtcaa atccctttcc aagtccgaca    4020
gtgggtacta tgctaatctc ttcttacata ttgggcttat gtccactgta gataagaagg    4080
ggaagaaagt gacatttgac aagctggaaa ggaagataag gagacttgat ctatctgtag    4140
ggcttagtga cgtgcttgga ccttccgtgc ttgtaaaggc gagaggtgca cggactaagc    4200
tgctggcacc tttcttctct agcagtggga cagcctgcta tcccatagca aatgcctctc    4260
ctcaggtggc caagatactc tggagccaaa ccgcgtgcct gcggagtgta aaagtcatta    4320
tccaagcggg cacccagcgt gctgtcgcag tgaccgccga ccacgaggtt acctctacta    4380
agctggagaa ggggcatacc attgccaaat acaatccctt caagaaatag gctgcatctc    4440
tgagattgca ctccgcccat cttccccggat caccatgaca ctaaataatg atctgtcttg    4500
attacttata gttagttcgc ctgtctatca aattagaaaa aacacgggta gaagattctg    4560
gatcccggtc ggcgccttca aggtgcaaga tgggctccag atcttctacc aggatcccag    4620
tacctcttat gctgaccgtc cgagtcatgt tggcactgag ttgcgtctgt ccgaccagcg    4680
cccttgatgg caggcctctt gcagctgcag ggattgtggt aacaggagac aaagcagtca    4740
```

```
atatatacac ctcatctcag acagggtcaa tcataatcaa gttactccca aatatgccca    4800
aggataaaga ggcgtgtgca aaagccccgt tggaggcata caacaggaca ttgactactt    4860
tgctcacccc ccttggtgat tctatccgta ggatacaaga gtctgtgacc acgtccggag    4920
gagggaaaca gagacgtctt ataggcgcca ttatcggtgg tgtagctctc ggggttgcaa    4980
ccgctgcaca gataacagca gcctcggctc tgatacaagc caatcaaaat gctgccaaca    5040
tactccggct aaaagagagc attgctgcaa ccaatgaggc tgtgcacgag gtcactaatg    5100
gattatcaca actagcagtg gcagttggga agatgcagca atttgttaat gaccagttta    5160
ataaaacagc tcaggaattg gactgtataa aaattacaca gcaggttggt gtagaactca    5220
acctgtacct aactgaattg actacagtat tcgggccaca aatcacttcc cctgccttaa    5280
ctcagctgac tatccaggcg ctttacaatc tagctggtgg gaatatggat tacttgttga    5340
ctaagttagg tgtggggaac aaccaactca gctcattaat tagtagtggc ctgatcaccg    5400
gcaaccctat tctgtacgac tcacagactc aactcttggg tatacaggta accctaccct    5460
cagtcgggaa cctaaataat atgcgtgcca cctacctgga aaccttgtct gtaagtacaa    5520
ccaaaggatt tgcctcagca cttgtcccaa agtagtgac acaggtcggt tccgtgatag    5580
aagagcttga cacctcgtac tgtatagaga ccgatttgga tctatattgt acaagaatag    5640
tgacattccc tatgtctcct ggtatttatt cctgtttgag tggcaataca tctgcttgca    5700
tgtactcaaa gactgaaggc gcattcacta cgccgtatat gaccctcaaa ggctcagtta    5760
ttgctaactg taagatgaca acatgtagat gtgcagaccc cccgggtatc atatcgcaaa    5820
attatggaga agctgtgtct ctaatagata ggcaatcatg caatatctta tccttagacg    5880
ggataacttt gaggctcagt ggggaattg atgcaactta tcaaaagaat atctcaatac    5940
aagattctca gtaatagtg acaggcaatc ttgatatctc gactgagctt gggaatgtca    6000
acaactcgat aagtaatgct ttggataagt tagaggaaag caacagcaaa ctagataagg    6060
tcaatgtcaa actgaccagc acatccgctc ttattaccta tatcgtttta actgtcatat    6120
ctcttgtatg tggtatactt agcctggttc tagcatgcta cctgatgtac aagcaaaagg    6180
cgcaacagaa gaccttgttg tggcttggga ataatacccct agaccagatg agggccacta    6240
caaaaatgtg aatacggatg agaggcagaa acatccccaa tagcagtttg tgtgtaaagt    6300
ctgacagcct gttaattaga agaattaaga aaaactacc ggatgtagat gaccaaaggg    6360
cgatatacgg gtagaacggt cggggaggcc gtccctcaat cgggagccgg gcctcacaac    6420
atccgttcta ccgcatcacc aatagcagtt ttcagtcatg gaccgcgcag ttagccaagt    6480
tgcgctagag aatgatgaaa gagaggcaaa gaatacatgg cgcttggtat tccggatcgc    6540
aatcctactc tcaacggtgg tgaccttagc catctctgca gccgcccttg catatagcat    6600
ggaggccagc acacctagcg atcttgtagg cataccgact gcgatctcta gagcagagga    6660
aaagattaca tctgcactcg gttccaatca agatgtagta gataggatat ataagcaggt    6720
ggccctcgaa tctccactgg cattgctaaa caccgaatct acaattatga acgcaataac    6780
gtctctctct tatcaaatca gtggggccgc aagtagcagc ggatgtggag cacccattca    6840
tgatcctgat tatattggag gaataggtaa agaacttatt gtagatgatg ctagcgacgt    6900
cacatcatac tatccctctg cgttccaaga cacctgaac tttatcccgg cgcctactac    6960
aggatcaggt tgcactcgga tgccctcatt tgacatgagc gctacccact actgttatac    7020
tcacaatgtg atattatctg gctgcagaga tcactcgcac tcacatcaat atttagcact    7080
```

-continued

```
tggtgtgctt cggacatctg caacagggag ggtattcttt tccactctgc gttccatcaa    7140
tctggatgac acccaaaatc ggaagtcttg cagtgtgagt gcaaccccct tgggttgtga    7200
tatgctgtgc tctaaagtca cagagactga agaagaggat tataactcag ctatccccac    7260
gtcgatggta catggaaggt tagggttcga cggccaatac cacgagaagg acctagatgt    7320
cacaacacta ttcgaggact gggtggcaaa ctacccagga gtaggaggcg gtcttttat    7380
tgacaaccgc gtatggttcc cagtttacgg agggctaaaa cccaattcgc ccagtgacac    7440
cgcacaagaa gggaaatatg taatatacaa gcgatacaat gacacatgtc cagatgagca    7500
agattatcag attcaaatgg ctaagtcttc atataagcct gggcggtttg gagggaaacg    7560
cgtacagcag gccatcttat ctatcaaagt gtcaacatcc ttgggcgagg acccggtgct    7620
gactgtaccg cccaacacag taacactcat ggggccgaa gcagagttc tcacagtagg    7680
gacatctcat ttcctttatc agcgagggtc atcatacttc tcccctgccc tactatatcc    7740
tatgatagtc agcaacaaaa cagccactct tcatagtcca tatacattca atgccttcac    7800
tcgaccaggt agtgtcccct tgccaggctt agcaagatgc cctaactcat gtgttaccgg    7860
agtctatact gatccatatc ccttggtctt ctataggaac cacaccttgc gaggggtatt    7920
cgggacgatg cttgatgata acaagcaag actcaaccct gtatctgcag tatttgacag    7980
catatcccgc agtcgcataa cccgggtgag ttcaagcagc accaaggcag catacacaac    8040
atcaacatgt tttaaagttg taaagaccaa taaaacctat tgtctcagca ttgccgaaat    8100
atccaatacc ctcttcgggg aattcagaat cgtcccttta ctagttgaga ttctcaagga    8160
tgatgggggtt agagaagcca ggtctagccg gttgagtcaa ctgcgagagg gttggaaaga    8220
tgacattgta tcacctatct tttgcgacgc caagaatcaa actgaatacc ggcacgagct    8280
cgagtcctac gctgccagtt ggccataatc agctagtgct aatgtgatta gattaagtct    8340
tgtcggtagt cacttgatta agaaaaatg tgggtggtag cgggatataa ggcaaaacaa    8400
ctcaaggagg atagcacggg taggacatgg cgagctccgg tcccgagagg gcggagcatc    8460
agattatcct accagagtca cacctgtctt caccattagt caagcacaaa ctactctatt    8520
actggaaatt aactgggcta ccactccctg acgagtgtga cttcgaccac ctcattctca    8580
gccgacaatg gaagaaaata cttgaatcgg cctcccctga cactgagaga atgataaaac    8640
ttggaagggc agtgcaccag actctcaacc acaattccaa gataaccgga gtactccatc    8700
ccaggtgttt agaagaattg gctagtattg aggttcctga ctcaaccaac aagtttcgga    8760
agatcgagaa gaaaatccaa attcacaaca caaggtatgg agaactgttc acaagactgt    8820
gcacgcatgt agagaagaaa ttgttgggat catcttggtc taataatgtc ccccggtcag    8880
aagagttcaa cagcatccgt acagatccgg cattctggtt tcactcaaaa tggtccacaa    8940
ctaagtttgc atggctccat ataaaacaga ttcaaaggca tctgattgtg gcagcaagaa    9000
caaggtccgc agccaacaaa ttggtgacgc tgacccataa ggtaggccaa gtctttgtta    9060
ctcctgagct tgtcattgtg acacatacag atgagaacaa gttcacgtgt cttacccagg    9120
aacttgtgtt gatgtatgca gatatgatgg agggcagaga tatggtcaac ataatatcat    9180
ccacggcggc acatctcagg agcctatcag agaaaattga tgacattctg cggttagtag    9240
atgccctggc aaaagatctg ggtaatcaag tctacgatgt tgtagcactc atggagggat    9300
ttgcatacgg cgccgtccag ctgcttgagc cgtcaggtac attcgcaggg gatttcttcg    9360
cattcaacct gcaggagctc aaagacactt tgatcggcct ccttcctaag gatatagcag    9420
aatctgtgac tcacgcaata gccactgtat tctctggctt agaacaaaat caagcggctg    9480
```

```
agatgctgtg cctgttgcgt ctatggggcc acccattact tgagtcccgt attgcggcaa    9540
aagcagtaag gagccaaatg tgcgcaccaa aaatggtaga ctttgatatg atcctccagg    9600
tattgtcttt cttttaaagga acaatcatca acggatacag aaagaagaat gcaggtgttt   9660
ggccacgtgt caaagtagat acgatatacg ggaaggtcat tgggcagcta cacgctgatt   9720
cagcggagat ttcacacgat atcatgttga gagagtacaa gagtttatct gcgcttgaat   9780
tcgagccatg tatagaatac gaccctatca ccaatctgag catgtttcta aaagacaagg   9840
cgatcgcaca cccgaaagac aactggctcg cctcgtttag gcgaaacctt ctctctgagg   9900
accagaagaa acatgtaaag gaggcaacct ctactaaccg tctcttgata gagttcttaa   9960
agtcaaatga ttttgatcca tataaggaga tggaatatct gacgacccct tgagtaccta   10020
gagatgacaa tgtggcagta tcatactcgc tcaaggagaa ggaagtgaag gttaatgggc   10080
ggattttgc taagctaaca aagaaattaa ggaactgtca agtgatggcg aagggatct   10140
tagctgacca gattgcacct ttctttcaag ggaatggggt cattcaggat agcatatctt   10200
taaccaagag tatgctagcg atgagtcaat tgtctttcaa cagcaataag aaacgtatca   10260
ctgactgcaa agaaagagta gcctcaaacc gcaatcacga tcaaaagagc aagaatcgtc   10320
ggagagttgc cacttttata acgactgacc tgcaaaagta ctgtcttaat tggagatatc   10380
agacagtcaa actgttcgct catgccatca atcagctgat gggcttacct cacttcttcg   10440
aatggattca tctaagacta atggatacta cgatgtttgt aggagaccct ttcaatcccc   10500
caagtgaccc aactgactgt gatctctcaa gagtcccaaa tgatgacata tatattgtca   10560
gtgctagagg gggtattgag ggattatgtc agaagctatg gacaatgatc tcaattgctg   10620
caatccaact gctgcagca agatcacatt gtcgcgtcgc ctgtatggta cagggtgaca   10680
atcaagtaat agctgtaacg agagaggtaa ggtcagatga ctccccggaa atggtgttaa   10740
cacaattgca tcaagccagt gataatttct tcaaggaatt gattcatgtt aatcatttga   10800
ttggccataa tttgaaggat cgtgaaacaa tcagatcaga cacattcttc atatacagca   10860
aacgaatatt caaagatgga gcaatactca gtcaagtcct caaaaattca tctaaattag   10920
tgctaatatc aggcgacctt agtgaaaaca ccgtaatgtc ctgtgccaac attgcatcta   10980
ctatagcacg gctgtgcgag aacgggcttc caaaggattt ctgttattac ttaaactacc   11040
tgatgagttg cgtgcagaca tactttgatt ctgagttttc catcactaac agctcgcacc   11100
ccgattctaa ccagtcgtgg attgaagaca tctcttttgt gcactcatat gtcctgaccc   11160
ctgcccagct aggggactg agcaacctcc aatactcaag gctctacacg aggaacatcg   11220
gtgacccggg aactactgct tttgcagaga tcaagcgatt agaagcagtg gggttactaa   11280
gtcctagtat tatgactaac atcttaacta ggccgcctgg aaatgagat tgggccagtc   11340
tgtgtaacga cccttactct ttcaattttg agactgtcgc gagtccaaat attgtcctta   11400
agaaacatac acaaagagtc ctatttgaaa cttgttcaaa tcccttatta tctggcgtgc   11460
atacagagga taatgaggca gaagagaagg cgttggctga atttttactc aatcaagaag   11520
taattcatcc acgtgtcgcg catgctatca tggaagcaag ctctataggt aggaggaagc   11580
agattcaagg gcttgttgac acaacaaaca ccgtaatcaa gattgcattg actaggaggc   11640
cacttggcat caagaggctg atgcggatag ttaactactc gagcatgcat gcaatgctgt   11700
ttagagacga tgttttctca tctaacaggt ctaaccaccc cttagtttcc tctaatatgt   11760
gttctctgac gctagcagac tatgcacgga atagaagctg gtcaccattg acggggggta   11820
```

```
gaaagatact gggtgtatct aatcctgata ctatagaact tgtagagggt gagatcctta    11880
gcgtcagcgg aggatgcaca agatgtgaca gcggagatga acaattcact tggttccatc    11940
ttccgagcaa tatagaactg accgatgaca ccagcaagaa tcctccgatg agagtgccgt    12000
acctcgggtc aaagactcaa gagaggaggg ccgcctcgct tgcgaaaata gctcatatgt    12060
caccacatgt gaaagctgct ctaagggcat catccgtgtt gatctgggct tatggagaca    12120
acgaagtaaa ttggactgct gctcttaaaa ttgcaagatc tcggtgcaat ataaactcag    12180
agtatcttcg actattgtcc cccttaccca cagctgggaa tctccaacat agactggatg    12240
acggcataac tcagatgaca ttcacccctg catctctcta cagggtgtca ccttatattc    12300
acatatccaa tgattctcaa aggttattca cggaagaagg agtcaaagag ggaaatgtag    12360
tttatcagca aatcatgctc ttgggtttat ctctaatcga atcactcttc ccgatgacga    12420
caaccaggac atacgatgag atcacattgc acctccacag taaatttagc tgctgtatca    12480
gggaagcacc ggttgcagtt cctttcgagt tactcgggat ggcaccagaa ctaaggacag    12540
tgacctcaaa taagtttatg tatgatccta gtcctgtatc ggagggtgac tttgcgagac    12600
ttgacttagc tatctttaag agttatgagc ttaatctaga atcatatccc acgatcgagc    12660
taatgaacat tctttcaata tccagcggga agttaatcgg ccagtctgtg gtttcttatg    12720
atgaagatac ctccataaag aatgacgcca taatagtgta tgacaacacc cggaattgga    12780
tcagcgaagc tcagaattca gatgtggtcc gcctattcga gtatgcagca cttgaagtgc    12840
ttctcgactg ttcttatcag ctctactatc tgagagtaag aggcctagac aatatcgtgt    12900
tgtatatgag tgacttatat aagaaatatgc caggaattct actttccaac attgcagcta    12960
caatatctca tcccatcatt cattcaagat tgcatgcagt aggcctggtc aatcacgacg    13020
ggtcacacca acttgcggac acagatttca tcgaaatgtc tgcaaaacta ttagtctctt    13080
gcactcgacg cgtggtctca ggtttatatg cagggaataa gtatgatctg ctgttcccgt    13140
ctgtcttaga tgataccctg agtgagaaga tgcttcagct gatatctcgg ttatgctgcc    13200
tgtatacggt gctctttgct acaacaagag agatcccgaa aataagaggc ttatctgcag    13260
aagagaagtg ttcagtactt actgagtacc tactgtcaga tgctgtgaaa ccattactta    13320
gttctgagca agtgagctct atcatgtctc ctaacatagt tacgttccca gctaatctat    13380
attacatgtc tcggaagagc cttaatttga ttagggaaag agaggacagg gacactatct    13440
tggcattgtt gttcccccaa gagccactac ttgagttccc cttagtacaa gatattggcg    13500
ctcgagtgaa agatccattc acccgacaac ctgcggcgtt tttacaagaa ttagatttga    13560
gcgctccagc aaggtatgac gcatttacac ttagtcaggt tcattctgaa cacacatcac    13620
caaatccgga ggacgattac ttagtacgat acctgttcag aggaataggg accgcgtcct    13680
cctcttggta taaggcatct caccttcttt ctgtacctga ggtcagatgt gcaaggcacg    13740
ggaattcctt atacttggca gaaggaagcg gagccattat gagtcttctc gaactgcatg    13800
tgccgcatga gactatctat tacaatacgc tcttctcaaa cgagatgaac cccccacagc    13860
ggcatttcgg accgacccca acacagtttc tgaattcagt tgtttatagg aatctacagg    13920
cggaggtacc atgtaaggat ggatttgtcc aggagttccg tccattatgg agagagaata    13980
cagaagaaag cgatctgacc tcagataaag cagtgggtta catcacatct gcagtgccct    14040
accggtctgt atcattgctg cactgtgaca ttgagattcc tccaggatcc aatcaaagct    14100
tactggatca actggctacc aatctgtctc tgattgccat gcattctgta agggagggcg    14160
gggtcgtgat catcaaagtg ttgtatgcaa tgggatatta cttccatcta ctcatgaact    14220
```

```
tgttcactcc gtgttctacg aaaggatata ttctctctaa tggctatgca tgtagagggg   14280
atatggagtg ttacctggta tttgtcatgg gctatcgagg tgggcctaca tttgtacatg   14340
aggtagtgag gatggcaaaa actctagtgc agcggcacgg tacactttg tccaaatcag   14400 atgagatcac actgactagg ttatttacct cacagcggca gcgtgtaaca gacatcctat   14460
ccagtccttt accgagacta ataaagttct tgagaaagaa tatcgatact gcgctaattg   14520
aagccggggg acaacccgtc cgtccattct gtgcagagag cttggtgagg acactagcgg   14580
acacaactca gatgacccag atcatcgcta gtcacattga cacagtcatt cgatctgtga   14640
tctacatgga ggctgagggt gatctcgccg acacagtgtt cttatttacc ccctacaatc   14700
tctctacaga cggtaaaaag agaacatcac ttaaacagtg cacaaggcag atcttagagg   14760
tcacaatatt gggtcttaga gttgaaaatc tcaataaagt aggtgatgta gtcagtctag   14820
tacttaaagg tatgatttct ctggaggacc tgatccctct aagaacatac ttgaagcgta   14880
gtacctgccc taagtatttg aagtctgttc taggtattac taaactcaaa gaaatgttta   14940
cagacacctc cttattatac ttgactcgtg ctcaacaaaa attctacatg aaaactatag   15000
gcaacgcagt caagggatac tacagtaact gtgactctta aagataatca catattaata   15060
ggctcctttt ctagttaact gagcccttgt tgatttaatg atactatatt agaaaaaagt   15120
tgcactccga tcctttagga ctcgtgttcg aattcaaata attgtcttag aaaaagttg    15180 cgcgtaattg ttcttgaatg tagtcctgtc attcaccaaa tctttgtttg gtgggtcggc   15240
atggcatctc cacctcctcg cggtccgacc tgggcatccg aaggaggacg cacgtccact   15300
cggatggcta agggagggc actccgcggt cactgctaac aaagcccgaa aggaagctga   15360
gttggctgct gcaccgctga gcaataacta gcataacccc ttggggcctc taaacgggtc   15420
ttgaggggtt ttttgctgga gctgtcgacc gatgcccttg agagccttca acccagtcag   15480
ctccttccgg tgggcgcggg gcatgactat cgtcgccgca cttatgactg tcttctttat   15540
catgcaactc gtaggacagg tgccggcagc gctctgggtc attttcggcg aggaccgctt   15600
tcgctggagc gcgacgatga tcggcctgtc gcttgcggta ttcggaatct tgcacgccct   15660
cgctcaagcc ttcgtcactg gtcccgccac caaacgtttc ggcgagaagc aggccattat   15720
cgccggcatg gcggccgacg cgctgggcta cgtcttgctg gcgttcgcga cgcgaggctg   15780
gatggccttc cccattatga ttcttctcgc ttccggcggc atcgggatgc ccgcgttgca   15840
ggccatgctg tccaggcagg tagatgacga ccatcaggga cagcttcaag gatcgctcgc   15900
ggctcttacc agcctaactt cgatcactgg accgctgatc gtcacggcga tttatgccgc   15960
ctcggcgagc acatggaacg ggttggcatg gattgtaggc gccgccctat accttgtctg   16020
cctccccgcg ttgcgtcgcg gtgcatggag ccgggccacc tcgacctgaa tggaagccgg   16080
cggcacctcg ctaacggatt caccactcca agaattggag ccaatcaatt cttgcggaga   16140
actgtgaatg cgcaaaccaa cccttggcag aacatatcca tcgcgtccgc catctccagc   16200
agccgcacgc ggcgcatctc gggcagcgtt gggtcctggc cacgggtgcg catgatcgtg   16260
ctcctgtcgt tgaggacccg gctaggctgg cggggttgcc ttactggtta gcagaatgaa   16320
tcaccgatac gcgagcgaac gtgaagcgac tgctgctgca aaacgtctgc gacctgagca   16380
acaacatgaa tggtcttcgg tttccgtgtt tcgtaaagtc tggaaacgcg gaagtcagcg   16440
ccctgcacca ttatgttccg gatctgcatc gcaggatgct gctggctacc ctgtggaaca   16500
cctacatctg tattaacgaa gcgctggcat tgaccctgag tgattttcct ctggtcccgc   16560
```

```
cgcatccata ccgccagttg tttaccctca caacgttcca gtaaccgggc atgttcatca   16620
tcagtaaccc gtatcgtgag catcctctct cgtttcatcg gtatcattac ccccatgaac   16680
agaaatcccc cttacacgga ggcatcagtg accaaacagg aaaaaaccgc ccttaacatg   16740
gcccgcttta tcagaagcca gacattaacg cttctggaga aactcaacga gctggacgcg   16800
gatgaacagg cagacatctg tgaatcgctt cacgaccacg ctgatgagct ttaccgcagc   16860
tgcctcgcgc gtttcggtga tgacggtgaa aacctctgac acatgcagct cccggagacg   16920
gtcacagctt gtctgtaagc ggatgccggg agcagacaag cccgtcaggg cgcgtcagcg   16980
ggtgttggcg ggtgtcgggg cgcagccatg acccagtcac gtagcgatag cggagtgtat   17040
actggcttaa ctatgcggca tcagagcaga ttgtactgag agtgcaccat atgcggtgtg   17100
aaataccgca cagatgcgta aggagaaaat accgcatcag gcgctcttcc gcttcctcgc   17160
tcactgactc gctgcgctcg gtcgttcggc tgcggcgagc ggtatcagct cactcaaagg   17220
cggtaatacg gttatccaca gaatcagggg ataacgcagg aaagaacatg tgagcaaaag   17280
gccagcaaaa ggccaggaac cgtaaaaagg ccgcgttgct ggcgtttttc cataggctcc   17340
gcccccctga cgagcatcac aaaaatcgac gctcaagtca gaggtggcga acccgacag   17400 gactataaag ataccaggcg tttccccctg gaagctccct cgtgcgctct cctgttccga   17460
ccctgccgct taccggatac ctgtccgcct ttctcccttc gggaagcgtg gcgctttctc   17520
atagctcacg ctgtaggtat ctcagttcgg tgtaggtcgt tcgctccaag ctgggctgtg   17580
tgcacgaacc ccccgttcag cccgaccgct gcgccttatc cggtaactat cgtcttgagt   17640
ccaacccggt aagacacgac ttatcgccac tggcagcagc cactggtaac aggattagca   17700
gagcgaggta tgtaggcggt gctacagagt tcttgaagtg gtggcctaac tacggctaca   17760
ctagaaggac agtatttggt atctgcgctc tgctgaagcc agttaccttc ggaaaaagag   17820
ttggtagctc ttgatccggc aaacaaacca ccgctggtag cggtggtttt tttgtttgca   17880
agcagcagat tacgcgcaga aaaaaaggat ctcaagaaga tcctttgatc ttttctacgg   17940
ggtctgacgc tcagtggaac gaaaactcac gttaagggat tttggtcatg agattatcaa   18000
aaaggatctt cacctagatc cttttaaatt aaaaatgaag ttttaaatca atctaaagta   18060
tatatgagta aacttggtct gacagttacc aatgcttaat cagtgaggca cctatctcag   18120
cgatctgtct atttcgttca tccatagttg cctgactccc cgtcgtgtag ataactacga   18180
tacgggaggg cttaccatct ggccccagtg ctgcaatgat accgcgagac ccacgctcac   18240
cggctccaga tttatcagca ataaaccagc cagccggaag ggccgagcgc agaagtggtc   18300
ctgcaacttt atccgcctcc atccagtcta ttaattgttg ccgggaagct agagtaagta   18360
gttcgccagt taatagtttg cgcaacgttg ttgccattgc tgcaggcatc gtggtgtcac   18420
gctcgtcgtt tggtatggct tcattcagct ccggttccca acgatcaagg cgagttacat   18480 gatccccat gttgtgcaaa aaagcggtta gctccttcgg tcctccgatc gttgtcagaa   18540
gtaagttggc cgcagtgtta tcactcatgg ttatggcagc actgcataat tctcttactg   18600
tcatgccatc cgtaagatgc ttttctgtga ctggtgagta ctcaaccaag tcattctgag   18660
aatagtgtat gcggcgaccg agttgctctt gcccggcgtc aacacgggat aataccgcgc   18720
cacatagcag aactttaaaa gtgctcatca ttggaaaacg ttcttcgggg cgaaaactct   18780
caaggatctt accgctgttg agatccagtt cgatgtaacc cactcgtgca cccaactgat   18840
cttcagcatc ttttactttc accagcgttt ctgggtgagc aaaaacagga aggcaaaatg   18900
ccgcaaaaaa gggaataagg gcgacacgga aatgttgaat actcatactc ttcctttttc   18960
```

```
aatattattg aagcatttat cagggttatt gtctcatgag cggatacata tttgaatgta    19020
tttagaaaaa taaacaaata ggggttccgc gcacatttcc ccgaaaagtg ccacctgacg    19080
tctaagaaac cattattatc atgacattaa cctataaaaa taggcgtatc acgaggccct    19140
ttcgtcttca agaattctca tgtttgacag cttatcat                            19178

<210> SEQ ID NO 2
<211> LENGTH: 6876
<212> TYPE: DNA
<213> ORGANISM: Artificial Sequence
<220> FEATURE:
<223> OTHER INFORMATION: Helper plasmid 1: NP

<400> SEQUENCE: 2
agcttcgcca ccatggcgtc ttctgtattc gatgagtacg agcagctcct cgcggctcag      60
actcgcccca atggagctca tggcggagga gagaagggga gcaccttaaa ggtagaagtc     120
ccggtattca ctctcaacag tgatgaccca gaagatagat ggaactttgc agtgttttgt     180
cttcggattg ctgttagcga ggatgccaac aaaccactta ggcaaggtgc tctcatatct     240
ctcttatgtt cccactctca agtgatgagg aaccatgttg cccttgcggg gaaacagaat     300
gaggccacac tggctgttct tgagatcgat ggttttacca acggcgtgcc ccagttcaac     360
aacaggagtg gagtgtctga agagagagca cagagattta tgatgatagc agggtctctc     420
cctcgggcat gcagcaacgg tacccccgttc gtcacagctg gggttgaaga tgatgcacca     480
gaagacatta ctgataccct ggagaggatc ctctctatcc aggctcaagt atgggtcacg     540
gtggcaaagg ccatgactgc atatgagaca gcagatgagt cagaaacaag aagaatcaat     600
aagtacatgc agcaaggcag ggtccagaag aagtacatcc tccacccgt atgcaggagc     660 gcaatccaac tcacaatcag acagtctctg gcggtccgca tcttttttggt tagcgagctt     720 aagagaggcc gcaacacggc aggtgggacc tccacctatt acaacttggt gggggatgta     780
gactcataca tcaggaacac tgggctaact gcattcttcc tgacacttaa atatggaatt     840
aacaccaaga catcagccct tgcacttagc agcctctcag gcgatatcca gaaaatgaag     900
cagctcatgc gcttgtatcg gatgaaagga gataatgcgc cgtacatgac attgctcggt     960
gacagtgacc agatgagctt tgcacctgcc gagtatgcac aactttactc ctttgccatg    1020
ggtatggcat cagtcctaga taaaggaact agcaaatacc aatttgccag ggactttatg    1080
agcacatcat tctggagact tggagtagag tatgctcagg ctcaaggaag tagcatcaat    1140
gaggatatgc ccgccgagct aaagctaacc ccagcagcaa ggagaggcct ggcagctgct    1200
gcccaaagag tgtctgagga gccagcagc atggacatgc ccacccaaca gccggggtc    1260 ctcactggac tcagcgacgg aggctcccaa gcccccaag gtgcactgaa cagatcacaa    1320 ggcaaccgg acaccgggga cggggagacc caatttctgg atctgatgag agcggtggca    1380
aatagcatga gagaagcgcc aaactctgcg cagggcaccc ctccaccggg gcctccccca    1440
acccctgggc cctctcaaga caatgacacc gactgggggt actgataaga attctgcaga    1500
tatccagcac agtggcggcc gctcgagtct agagggcccg tttaaacccg ctgatcagcc    1560
tcgactgtgc cttctagttg ccagccatct gttgtttgcc cctcccccgt gccttccttg    1620
accctggaag gtgccactcc cactgtcctt tcctaataaa atgaggaaat tgcatcgcat    1680
tgtctgagta ggtgtcattc tattctgggg ggtggggtgg gcaggacag caaggggag    1740 gattgggaag acaatagcag gcatgctggg gatgcggtgg gctctatggc ttctgaggcg    1800
```

```
gaaagaacca gctggggctc tagggggtat ccccacgcgc cctgtagcgg cgcattaagc    1860 cggcgggtg tggtggttac gcgcagcgtg accgctacac ttgccagcgc cctagcgccc     1920
gctcctttcg cttcttccc ttcctttctc gccacgttcg ccggctttcc ccgtcaagct     1980
ctaaatcggg ggctcccttt agggttccga tttagtgctt tacggcacct cgaccccaaa    2040
aaacttgatt agggtgatgg ttcacgtagt gggccatcgc cctgatagac ggttttcgc     2100 cctttgacgt tggagtccac gttctttaat agtggactct tgttccaaac tggaacaaca    2160 ctcaaccta tctcggtcta ttcttttgat ttataaggga ttttgccgat ttcggcctat     2220
tggttaaaaa atgagctgat ttaacaaaaa tttaacgcga attaattctg tggaatgtgt    2280
gtcagttagg gtgtggaaag tccccaggct ccccagcagg cagaagtatg caaagcatgc    2340
atctcaatta gtcagcaacc aggtgtggaa agtccccagg ctccccagca ggcagaagta    2400
tgcaaagcat gcatctcaat tagtcagcaa ccatagtccc gccctaact  ccgcccatcc    2460 cgcccctaac tccgcccagt tccgcccatt ctccgcccca tggctgacta atttttttta    2520
tttatgcaga ggccgaggcc gcctctgcct ctgagctatt ccagaagtag tgaggaggct    2580 ttttttggagg cctaggcttt tgcaaaaagc tcccgggagc ttgtatatcc attttcggat   2640
ctgatcaaga gacaggatga ggatcgtttc gcatgattga acaagatgga ttgcacgcag    2700
gttctccggc cgcttgggtg gagaggctat tcggctatga ctgggcacaa cagacaatcg    2760
gctgctctga tgccgccgtg ttccggctgt cagcgcaggg gcgcccggtt cttttttgtca   2820 agaccgacct gtccggtgcc ctgaatgaac tgcaggacga ggcagcgcgg ctatcgtggc    2880
tggccacgac gggcgttcct tgcgcagctg tgctcgacgt tgtcactgaa gcgggaaggg    2940
actggctgct attgggcgaa gtgccggggc aggatctcct gtcatctcac cttgctcctg    3000
ccgagaaagt atccatcatg gctgatgcaa tgcggcggct gcatacgctt gatccggcta    3060
cctgcccatt cgaccaccaa gcgaaacatc gcatcgagcg agcacgtact cggatggaag    3120
ccggtcttgt cgatcaggat gatctggacg aagagcatca ggggctcgcg ccagccgaac    3180
tgttcgccag gctcaaggcg cgcatgcccg acggcgagga tctcgtcgtg acccatggcg    3240
atgcctgctt gccgaatatc atggtggaaa atggccgctt ttctggattc atcgactgtg    3300
gccggctggg tgtggcggac cgctatcagg acatagcgtt ggctacccgt gatattgctg    3360
aagagcttgg cggcgaatgg gctgaccgct tcctcgtgct ttacggtatc gccgctcccg    3420
attcgcagcg catcgccttc tatcgccttc ttgacgagtt cttctgagcg ggactctggg    3480
gttcgaaatg accgaccaag cgacgcccaa cctgccatca cgagatttcg attccaccgc    3540
cgccttctat gaaaggttgg gcttcggaat cgttttccgg gacgccggct ggatgatcct    3600
ccagcgcggg gatctcatgc tggagttctt cgcccacccc aacttgttta ttgcagctta    3660
taatggttac aaataaagca atagcatcac aaatttcaca ataaagcat tttttttcact    3720 gcattctagt tgtggtttgt ccaaactcat caatgtatct tatcatgtct gtataccgtc    3780
gacctctagc tagagcttgg cgtaatcatg gtcatagctg tttcctgtgt gaaattgtta    3840
tccgctcaca attccacaca acatacgagc cggaagcata agtgtaaag cctggggtgc     3900 ctaatgagtg agctaactca cattaattgc gttgcgctca ctgcccgctt ccagtcggg     3960 aaacctgtcg tgccagctgc attaatgaat cggccaacgc gcgggagag gcggtttgcg    4020 tattgggcgc tcttccgctt cctcgctcac tgactcgctg cgctcggtcg ttcggctgcg    4080
gcgagcggta tcagctcact caaaggcggt aatacggtta tccacagaat cagggataa    4140 cgcaggaaag aacatgtgag caaaaggcca gcaaaaggcc aggaaccgta aaaaggccgc    4200
```

```
gttgctggcg ttttttccata ggctccgccc ccctgacgag catcacaaaa atcgacgctc   4260
aagtcagagg tggcgaaacc cgacaggact ataaagatac caggcgtttc ccctggaag    4320 ctccctcgtg cgctctcctg ttccgaccct gccgcttacc ggatacctgt ccgcctttct   4380
cccttcggga agcgtggcgc tttctcatag ctcacgctgt aggtatctca gttcggtgta   4440
ggtcgttcgc tccaagctgg gctgtgtgca cgaaccccc gttcagcccg accgctgcgc    4500
cttatccggt aactatcgtc ttgagtccaa cccggtaaga cacgacttat cgccactggc   4560
agcagccact ggtaacagga ttagcagagc gaggtatgta ggcggtgcta cagagttctt   4620
gaagtggtgg cctaactacg gctacactag aagaacagta tttggtatct gcgctctgct   4680
gaagccagtt accttcggaa aaagagttgg tagctcttga tccggcaaac aaaccaccgc   4740
tggtagcggt ttttttgttt gcaagcagca gattacgcgc agaaaaaaag gatctcaaga   4800
agatcctttg atcttttcta cggggtctga cgctcagtgg aacgaaaact cacgttaagg   4860
gattttggtc atgagattat caaaaaggat cttcacctag atccttttaa attaaaatg    4920 aagttttaaa tcaatctaaa gtatatatga gtaaacttgg tctgacagtt accaatgctt   4980
aatcagtgag gcacctatct cagcgatctg tctatttcgt tcatccatag ttgcctgact   5040
ccccgtcgtg tagataacta cgatacggga gggcttacca tctggcccca gtgctgcaat   5100
gataccgcga gacccacgct caccggctcc agatttatca gcaataaacc agccagccgg   5160
aagggccgag cgcagaagtg gtcctgcaac tttatccgcc tccatccagt ctattaattg   5220
ttgccgggaa gctagagtaa gtagttcgcc agttaatagt ttgcgcaacg ttgttgccat   5280
tgctacaggc atcgtggtgt cacgctcgtc gtttggtatg gcttcattca gctccggttc   5340
ccaacgatca aggcgagtta catgatcccc catgttgtgc aaaaaagcgg ttagctcctt   5400
cggtcctccg atcgttgtca gaagtaagtt ggccgcagtg ttatcactca tggttatggc   5460
agcactgcat aattctctta ctgtcatgcc atccgtaaga tgcttttctg tgactggtga   5520
gtactcaacc aagtcattct gagaatagtg tatgcggcga ccgagttgct cttgcccggc   5580
gtcaatacgg gataataccg cgccacatag cagaacttta aaagtgctca tcattggaaa   5640
acgttcttcg gggcgaaaac tctcaaggat cttaccgctg ttgagatcca gttcgatgta   5700
acccactcgt gcacccaact gatcttcagc atcttttact ttcaccagcg tttctgggtg   5760
agcaaaaaca ggaaggcaaa atgccgcaaa aaagggaata agggcgacac ggaaatgttg   5820
aatactcata ctcttccttt ttcaatatta ttgaagcatt tatcagggtt attgtctcat   5880
gagcggatac atatttgaat gtatttagaa aaataaacaa ataggggttc cgcgcacatt   5940
tccccgaaaa gtgccacctg acgtcgacgg atcgggagat ctcccgatcc cctatggtgc   6000
actctcagta caatctgctc tgatgccgca tagttaagcc agtatctgct ccctgcttgt   6060
gtgttggagg tcgctgagta gtgcgcgagc aaaatttaag ctacaacaag gcaaggcttg   6120
accgacaatt gcatgaagaa tctgcttagg gttaggcgtt ttgcgctgct tcgcgatgta   6180
cgggccagat atacgcgttg acattgatta ttgactagtt attaatagta atcaattacg   6240
gggtcattag ttcatagccc atatatggag ttccgcgtta cataacttac ggtaaatggc   6300
ccgcctggct gaccgcccaa cgacccccgc ccattgacgt caataatgac gtatgttccc   6360
atagtaacgc caatagggac tttccattga cgtcaatggg tggagtattt acggtaaact   6420
gcccacttgg cagtacatca agtgtatcat atgccaagta cgccccctat tgacgtcaat   6480
gacggtaaat ggcccgcctg gcattatgcc cagtacatga cctatgggac tttcctact    6540
```

| | |
|---|---|
| tggcagtaca tctacgtatt agtcatcgct attaccatgg tgatgcggtt ttggcagtac | 6600 |
| atcaatgggc gtggatagcg gtttgactca cggggatttc caagtctcca ccccattgac | 6660 |
| gtcaatggga gtttgttttg gcaccaaaat caacgggact ttccaaaatg tcgtaacaac | 6720 |
| tccgccccat tgacgcaaat gggcggtagg cgtgtacggt gggaggtcta tataagcaga | 6780 |
| gctctctggc taactagaga acccactgct tactggctta tcgaaattaa tacgactcac | 6840 |
| tatagggaga cccaagctgg ctagcgttta aactta | 6876 |

<210> SEQ ID NO 3
<211> LENGTH: 6597
<212> TYPE: DNA
<213> ORGANISM: Artificial Sequence
<220> FEATURE:
<223> OTHER INFORMATION: Helper plasmid 2: P

<400> SEQUENCE: 3

| | |
|---|---|
| agcttcgcca ccatggagat ggccaccttt acagatgcgg agatcgacga gctatttgag | 60 |
| accagtggaa ctgtcattga cagcataatt acggcccagg gaaaaccagt agagactgtt | 120 |
| ggaaggagtg caatcccaca aggcaaaact aaggctttga gcgcagcatg ggagaagcat | 180 |
| gggagcatcc agtcaccagc cagccaagac acccctgatc gacaggacag atcagataaa | 240 |
| caactgtcca cacccgagca agcgagtcca acgacagcc cccagccac atccactgac | 300 |
| cagcctccca ctcaggctgc agatgaggcc ggcgatacac agctcaagac cggagcaagc | 360 |
| aactctctgc tgtcgatgct tgataaactc agcaataagt catctaatgc taaaaagggc | 420 |
| ccagggtcga gccctcaaga aaggcatcat caacgtctga ctcaacaaca ggggagtcaa | 480 |
| caaagccgcg gaaacagcca gagagaccg cagaaccagg ccaaggccat ccctggaaac | 540 |
| caggtcacag acgcgaacac agcatatcat ggacaatggg aggagtcaca actatcagct | 600 |
| ggtgcaaccc atcatgctct ccgatcagag cagagccaag acaatactcc tgcacctgtg | 660 |
| gatcatgtcc agctacctgt cgactttgtg caggcgatga tgtctatgat ggaggcgata | 720 |
| tcacagaggg taagtaaagt tgactatcag ctggaccttg tcttgaaaca gacatcttct | 780 |
| atccccatga tgcggtctga aatccagcag ctgaaaacgt ctgttgcggt catggaagcc | 840 |
| aatttgggca tgatgaagat cctggaccct ggttgtgcca acgtttcatc tctaagtgat | 900 |
| ctacgggcag ttgcccgatc ccacccggtt ttaatttctg gccccggaga cccatctcct | 960 |
| tatgtgaccc aaggggggcga atggcactc aataaacttt cgcaaccggt gcaacacccc | 1020 |
| tctgaattga ttaaacccgc cacggcaagc gggcctgata taggagtgga gaaagacact | 1080 |
| gtccgtgcat tgatcatgtc acgccctatg catccgagct cttcagctag gctcttgagc | 1140 |
| aaactgacg cagccggatc gattgaggaa atcagaaaaa tcaagcgcct tgcactgaat | 1200 |
| ggctaataag aattctgcag atatccagca cagtggcggc cgctcgagtc tagagggccc | 1260 |
| gtttaaaccc gctgatcagc ctcgactgtg ccttctagtt gccagccatc tgttgtttgc | 1320 |
| ccctcccccg tgccttcctt gaccctggaa ggtgccactc ccactgtcct ttcctaataa | 1380 |
| aatgaggaaa ttgcatcgca ttgtctgagt aggtgtcatt ctattctggg gggtggggtg | 1440 |
| gggcaggaca gcaaggggga ggattgggaa gacaatagca ggcatgctgg ggatgcggtg | 1500 |
| ggctctatgg cttctgaggc ggaaagaacc agctggggct ctaggggggta tccccacgcg | 1560 |
| ccctgtagcg gcgcattaag cgcggcgggt gtggtggtta cgcgcagcgt gaccgctaca | 1620 |
| cttgccagcg ccctagcgcc cgctcctttc gctttcttcc cttcctttct cgccacgttc | 1680 |
| gccggctttc cccgtcaagc tctaaatcgg gggctccctt tagggttccg atttagtgct | 1740 |

```
ttacggcacc tcgaccccaa aaaacttgat tagggtgatg gttcacgtag tgggccatcg    1800
ccctgataga cggttttttcg cccttttgacg ttggagtcca cgttctttaa tagtggactc   1860
ttgttccaaa ctggaacaac actcaaccct atctcggtct attcttttga tttataaggg    1920
attttgccga tttcggccta ttggttaaaa aatgagctga tttaacaaaa atttaacgcg    1980
aattaattct gtggaatgtg tgtcagttag ggtgtggaaa gtccccaggc tccccagcag    2040
gcagaagtat gcaaagcatg catctcaatt agtcagcaac caggtgtgga aagtccccag    2100
gctccccagc aggcagaagt atgcaaagca tgcatctcaa ttagtcagca accatagtcc    2160
cgcccctaac tccgcccatc ccgcccctaa ctccgcccag ttccgcccat tctccgcccc    2220
atggctgact aattttttttt atttatgcag aggccgaggc cgcctctgcc tctgagctat    2280
tccagaagta gtgaggaggc tttttttggag gcctaggctt ttgcaaaaag ctcccgggag    2340
cttgtatatc cattttcgga tctgatcaag agacaggatg aggatcgttt cgcatgattg    2400
aacaagatgg attgcacgca ggttctccgg ccgcttgggt ggagaggcta ttcggctatg    2460
actgggcaca acagacaatc ggctgctctg atgccgccgt gttccggctg tcagcgcagg    2520
ggcgcccggt tctttttttgtc aagaccgacc tgtccggtgc cctgaatgaa ctgcaggacg    2580
aggcagcgcg gctatcgtgg ctggccacga cgggcgttcc ttgcgcagct gtgctcgacg    2640
ttgtcactga agcgggaagg gactggctgc tattgggcga agtgccgggg caggatctcc    2700
tgtcatctca ccttgctcct gccgagaaag tatccatcat ggctgatgca atgcggcggc    2760
tgcatacgct tgatccggct acctgcccat tcgaccacca agcgaaacat cgcatcgagc    2820
gagcacgtac tcggatggaa gccggtcttg tcgatcagga tgatctggac gaagagcatc    2880
aggggctcgc gccagccgaa ctgttcgcca ggctcaaggc gcgcatgccc gacggcgagg    2940
atctcgtcgt gacccatggc gatgcctgct tgccgaatat catggtggaa aatggccgct    3000
tttctggatt catcgactgt ggccggctgg gtgtggcgga ccgctatcag gacatagcgt    3060
tggctacccg tgatattgct gaagagcttg gcggcgaatg ggctgaccgc ttcctcgtgc    3120
tttacggtat cgccgctccc gattcgcagc gcatcgcctt ctatcgcctt cttgacgagt    3180
tcttctgagc gggactctgg ggttcgaaat gaccgaccaa gcgacgccca acctgccatc    3240
acgagatttc gattccaccg ccgccttcta tgaaaggttg gcttcggaa tcgttttccg     3300 ggacgccggc tggatgatcc tccagcgcgg ggatctcatg ctggagttct cgcccaccc     3360 caacttgttt attgcagctt ataatggtta caaataaagc aatagcatca caaatttcac    3420
aaataaagca tttttttcac tgcattctag ttgtggtttg tccaaactca tcaatgtatc    3480
ttatcatgtc tgtataccgt cgacctctag ctagagcttg gcgtaatcat ggtcatagct    3540
gtttcctgtg tgaaattgtt atccgctcac aattccacac aacatacgag ccggaagcat    3600
aaagtgtaaa gcctggggtg cctaatgagt gagctaactc acattaattg cgttgcgctc    3660
actgcccgct ttccagtcgg gaaacctgtc gtgccagctg cattaatgaa tcggccaacg    3720
cgcggggaga ggcggtttgc gtattgggcg ctcttccgct tcctcgctca ctgactcgct    3780
gcgctcggtc gttcggctgc ggcgagcggt atcagctcac tcaaaggcgg taatacggtt    3840
atccacagaa tcaggggata acgcaggaaa gaacatgtga gcaaaaggcc agcaaaaggc    3900
caggaaccgt aaaaaggccg cgttgctggc gttttttccat aggctccgcc cccctgacga    3960
gcatcacaaa aatcgacgct caagtcagag gtggcgaaac ccgacaggac tataaagata    4020
ccaggcgttt ccccctggaa gctccctcgt gcgctctcct gttccgaccc tgccgcttac    4080
```

```
cggatacctg tccgcctttc tcccttcggg aagcgtggcg ctttctcata gctcacgctg    4140
taggtatctc agttcggtgt aggtcgttcg ctccaagctg ggctgtgtgc acgaaccccc    4200
cgttcagccc gaccgctgcg ccttatccgg taactatcgt cttgagtcca acccggtaag    4260
acacgactta tcgccactgg cagcagccac tggtaacagg attagcagag cgaggtatgt    4320
aggcggtgct acagagttct tgaagtggtg gcctaactac ggctacacta agaacagt     4380 atttggtatc tgcgctctgc tgaagccagt taccttcgga aaaagagttg gtagctcttg    4440
atccggcaaa caaccaccg ctggtagcgg ttttttttgtt tgcaagcagc agattacgcg    4500
cagaaaaaaa ggatctcaag aagatccttt gatcttttct acggggtctg acgctcagtg    4560
gaacgaaaac tcacgttaag ggattttggt catgagatta caaaaagga tcttcaccta    4620 gatccttta aattaaaaat gaagttttaa atcaatctaa agtatatatg agtaaacttg    4680
gtctgacagt taccaatgct taatcagtga ggcacctatc tcagcgatct gtctatttcg    4740
ttcatccata gttgcctgac tccccgtcgt gtagataact acgatacggg agggcttacc    4800
atctggcccc agtgctgcaa tgataccgcg agacccacgc tcaccggctc cagatttatc    4860
agcaataaac cagccagccg gaagggccga gcgcagaagt ggtcctgcaa ctttatccgc    4920
ctccatccag tctattaatt gttgccggga agctagagta agtagttcgc cagttaatag    4980
tttgcgcaac gttgttgcca ttgctacagg catcgtggtg tcacgctcgt cgtttggtat    5040
ggcttcattc agctccggtt cccaacgatc aaggcgagtt acatgatccc ccatgttgtg    5100
caaaaaagcg gttagctcct tcggtcctcc gatcgttgtc agaagtaagt tggccgcagt    5160
gttatcactc atggttatgg cagcactgca taattctctt actgtcatgc catccgtaag    5220
atgcttttct gtgactggtg agtactcaac caagtcattc tgagaatagt gtatgcggcg    5280
accgagttgc tcttgcccgg cgtcaatacg ggataatacc gcgccacata gcagaacttt    5340
aaaagtgctc atcattggaa aacgttcttc ggggcgaaaa ctctcaagga tcttaccgct    5400
gttgagatcc agttcgatgt aacccactcg tgcacccaac tgatcttcag catcttttac    5460
tttcaccagc gtttctgggt gagcaaaaac aggaaggcaa aatgccgcaa aaaagggaat    5520
aagggcgaca cggaaatgtt gaatactcat actcttcctt tttcaatatt attgaagcat    5580
ttatcagggt tattgtctca tgagcggata catatttgaa tgtatttaga aaaataaaca    5640
aataggggtt ccgcgcacat ttccccgaaa agtgccacct gacgtcgacg gatcgggaga    5700
tctcccgatc ccctatggtg cactctcagt acaatctgct ctgatgccgc atagttaagc    5760
cagtatctgc tccctgcttg tgtgttggag gtcgctgagt agtgcgcgag caaaatttaa    5820
gctacaacaa ggcaaggctt gaccgacaat tgcatgaaga atctgcttag ggttaggcgt    5880
tttgcgctgc ttcgcgatgt acgggccaga tatacgcgtt gacattgatt attgactagt    5940
tattaatagt aatcaattac ggggtcatta gttcatagcc catatatgga gttccgcgtt    6000
acataactta cggtaaatgg cccgcctggc tgaccgccca acgacccccg cccattgacg    6060
tcaataatga cgtatgttcc catagtaacg ccaataggga ctttccattg acgtcaatgg    6120
gtggagtatt tacggtaaac tgcccacttg gcagtacatc aagtgtatca tatgccaagt    6180 acgccccta ttgacgtcaa tgacggtaaa tggcccgcct ggcattatgc ccagtacatg    6240
accttatggg actttcctac ttggcagtac atctacgtat tagtcatcgc tattaccatg    6300
gtgatgcggt tttggcagta catcaatggg cgtggatagc ggtttgactc acggggattt    6360
ccaagtctcc accccattga cgtcaatggg agtttgtttt ggcaccaaaa tcaacgggac    6420
tttccaaaat gtcgtaacaa ctccgcccca ttgacgcaaa tgggcggtag gcgtgtacgg    6480
```

-continued

```
tgggaggtct atataagcag agctctctgg ctaactagag aacccactgc ttactggctt    6540
atcgaaatta atacgactca ctatagggag acccaagctg gctagcgttt aaactta      6597
```

<210> SEQ ID NO 4
<211> LENGTH: 12041
<212> TYPE: DNA
<213> ORGANISM: Artificial Sequence
<220> FEATURE:
<223> OTHER INFORMATION: Helper plasmid 3: L

<400> SEQUENCE: 4

```
ggccgcgcca ccatggcgag ctccggtccc gagagggcgg agcatcagat tatcctacca      60
gagtcacacc tgtcttcacc attagtcaag cacaaactac tctattactg gaaattaact    120
gggctaccac tccctgacga gtgtgacttc gaccacctca ttctcagccg acaatggaag    180
aaaatacttg aatcggcctc ccctgacact gagagaatga taaaacttgg aagggcagtg    240
caccagactc tcaaccacaa ttccaagata accggagtac tccatcccag gtgtttagaa    300
gaattggcta gtattgaggt tcctgactca accaacaagt tcggaagat cgagaagaaa     360
atccaaattc acaacacaag gtatggagaa ctgttcacaa gactgtgcac gcatgtagag    420
aagaaattgt tgggatcatc ttggtctaat aatgtccccc ggtcagaaga gttcaacagc    480
atccgtacag atccggcatt ctggtttcac tcaaaatggt ccacaactaa gtttgcatgg    540
ctccatataa aacagattca aaggcatctg attgtggcag caagaacaag gtccgcagcc    600
aacaaattgg tgacgctgac ccataaggta ggccaagtct tgttactcc tgagcttgtc    660
attgtgacac atacagatga aacaagttc acgtgtctta cccaggaact tgtgttgatg    720
tatgcagata tgatggaggg cagagatatg gtcaacataa tatcatccac ggcggcacat    780
ctcaggagcc tatcagagaa aattgatgac attctgcggt tagtagatgc cctggcaaaa    840
gatctgggta tcaagtcta cgatgttgta gcactcatgg agggatttgc atacggcgcc    900
gtccagctgc ttgagccgtc aggtacattc gcaggggatt tcttcgcatt caacctgcag    960
gagctcaaag acactttgat cggcctcctt cctaaggata tagcagaatc tgtgactcac   1020
gcaatagcca ctgtattctc tggcttagaa caaaatcaag cggctgagat gctgtgcctg   1080
ttgcgtctat ggggccaccc attacttgag tcccgtattg cggcaaaagc agtaaggagc   1140
caaatgtgcg caccaaaaat ggtagacttt gatatgatcc tccaggtatt gtctttcttt   1200
aaaggaacaa tcatcaacgg atacagaaag aagaatgcag gtgtttggcc acgtgtcaaa   1260
gtagatacga tatacgggaa ggtcattggg cagctacacg ctgattcagc ggagatttca   1320
cacgatatca tgttgagaga gtacaagagt ttatctgcgc ttgaattcga gccatgtata   1380
gaatacgacc ctatcaccaa tctgagcatg tttctaaaag acaaggcgat cgcacacccg   1440
aaagacaact ggctcgcctc gtttaggcga aaccttctct ctgaggacca agagaaacat   1500
gtaaaggagg caacctctac taaccgtctc ttgatagagt tcttaaagtc aaatgatttt   1560
gatccatata aggagatgga atatctgacg acccttgagt acctaagaga tgacaatgtg   1620
gcagtatcat actcgctcaa ggagaaggaa gtgaaggtta atgggcggat tttttgctaag   1680
ctaacaaaga aattaaggaa ctgtcaagtg atggcggaag gatcttagc tgaccagatt    1740
gcacctttct ttcaagggaa tgggtcatt caggatagca tatctttaac caagagtatg   1800
ctagcgatga gtcaattgtc tttcaacagc aataagaaac gtatcactga ctgcaaagaa   1860
agagtagcct caaaccgcaa tcacgatcaa aagagcaaga atcgtcggag agttgccact   1920
```

```
tttataacga ctgacctgca aaagtactgt cttaattgga gatatcagac aatcaaactg    1980
ttcgctcatg ccatcaatca gctgatgggc ttacctcact tcttcgaatg gattcatcta    2040
agactaatgg atactacgat gtttgtagga gacccttca atcccccaag tgacccaact     2100
gactgtgatc tctcaagagt cccaaatgat gacatatata ttgtcagtgc tagagggggt    2160
attgagggat tatgtcagaa gctatggaca atgatctcaa ttgctgcaat ccaacttgct    2220
gcagcaagat cacattgtcg cgtcgcctgt atggtacagg gtgacaatca agtaatagct    2280
gtaacgagag aggtaaggtc agatgactcc ccggaaatgg tgttaacaca attgcatcaa    2340
gccagtgata atttcttcaa ggaattgatt catgttaatc atttgattgg ccataatttg    2400
aaggatcgtg aaacaatcag atcagacaca ttcttcatat acagcaaacg aatattcaaa    2460
gatggagcaa tactcagtca gtcctcaaa aattcatcta aattagtgct aatatcaggc     2520
gaccttagtg aaaacaccgt aatgtcctgt gccaacattg catctactat agcacggctg    2580
tgcgagaacg ggcttccaaa ggatttctgt tattacttaa actacctgat gagttgcgtg    2640
cagacatact ttgattctga gttttccatc actaacagct cgcaccccga ttctaaccag    2700
tcgtggattg aagacatctc ttttgtgcac tcatatgtcc tgacccctgc ccagctaggg    2760
ggactgagca acctccaata ctcaaggctc tacacgagga acatcggtga cccgggaact    2820
actgcttttg cagagatcaa gcgattagaa gcagtggggt tactaagtcc tagtattatg    2880
actaacatct taactaggcc gcctggaaat ggagattggg ccagtctgtg taacgaccct    2940
tactctttca attttgagac tgtcgcgagt ccaaatattg tccttaagaa acatacacaa    3000
agagtcctat ttgaaacttg ttcaaatccc ttattatctg gcgtgcatac agaggataat    3060
gaggcagaag agaaggcgtt ggctgaattt ttactcaatc aagaagtaat tcatccacgt    3120
gtcgcgcatg ctatcatgga agcaagctct ataggtagga ggaagcagat tcaagggctt    3180
gttgacacaa caaacaccgt aatcaagatt gcattgacta ggaggccact tggcatcaag    3240
aggctgatgc ggatagttaa ctactcgagc atgcatgcaa tgctgtttag agacgatgtt    3300
ttctcatcta acaggtctaa ccacccctta gtttcctcta atatgtgttc tctgacgcta    3360
gcagactatg cacggaatag aagctggtca ccattgacgg ggggtagaaa gatactgggt    3420
gtatctaatc ctgatactat agaacttgta gagggtgaga tccttagcgt cagcggagga    3480
tgcacaagat gtgacagcgg agatgaacaa ttcacttggt tccatcttcc gagcaatata    3540
gaactgaccg atgacaccag caagaatcct ccgatgagag tgccgtacct cgggtcaaag    3600
actcaagaga ggagggccgc ctcgcttgcg aaaatagctc atatgtcacc acatgtgaaa    3660
gctgctctaa gggcatcatc cgtgttgatc tgggcttatg gagacaacga agtaaattgg    3720
actgctgctc ttaaaattgc aagatctcgg tgcaatataa actcagagta tcttcgacta    3780
ttgtccccct tacccacagc tgggaatctc caacatagac tggatgacgg cataactcag    3840
atgacattca cccctgcatc tctctacagg gtgtcacctt atattcacat atccaatgat    3900
tctcaaaggt tattcacgga agaaggagtc aaagagggaa atgtagttta tcagcaaatc    3960
atgctcttgg gtttatctct aatcgaatca ctcttcccga tgacgacaac caggacatac    4020
gatgagatca cattgcacct ccacagtaaa tttagctgct gtatcaggga agcaccggtt    4080
gcagttcctt tcgagttact cgggatggca ccagaactaa ggacagtgac ctcaaataag    4140
tttatgtatg atcctagtcc tgtatcggag ggtgactttg cgagacttga cttagctatc    4200
tttaagagtt atgagcttaa tctagaatca tatcccacaa tcgagctaat gaacattctt    4260
tcaatatcca gcgggaagtt aatcggccag tctgtggttt cttatgatga agatacctcc    4320
```

```
ataaagaatg acgccataat agtgtatgac aacacccgga attggatcag cgaagctcag   4380
aattcagatg tggtccgcct attcgagtat gcagcacttg aagtgcttct cgactgttct   4440
tatcagctct actatctgag agtaagaggc ctagacaata tcgtgttgta tatgagtgac   4500
ttatataaga atatgccagg aattctactt tccaacattg cagctacaat atctcatccc   4560
atcattcatt caagattgca tgcagtaggc ctggtcaatc acgacgggtc acaccaactt   4620
gcagacacag atttcatcga aatgtctgca aaactattag tctcttgcac tcgacgcgtg   4680
gtctcaggtt tatatgcagg gaataagtat gatctgctgt tcccgtctgt cttagatgat   4740
aacctgagtg agaagatgct tcagctgata tctcggttat gctgcctgta tacggtgctc   4800
tttgctacaa caagagagat cccgaaaata agaggcttat ctgcagaaga gaagtgttca   4860
gtacttactg agtacctact gtcagatgct gtgaaaccat tacttagttc tgagcaagtg   4920
agctctatca tgtctcctaa catagttacg ttcccagcta atctatatta catgtctcgg   4980
aagagcctta atttgattag ggaaagagag acagggaca ctatcttggc attgttgttc   5040
ccccaagagc cactacttga gttcccctta gtacaagata ttggcgctcg agtgaaagat   5100
ccattcaccc gacaacctgc ggcgttttta caagaattag atttgagcgc tccagcaagg   5160
tatgacgcat ttacacttag tcaggttcat tctgaacaca catcaccaaa tccggaggac   5220
gattacttag tacgatacct gttcagagga ataggaccg cgtcctcctc ttggtataag   5280
gcatctcacc ttctttctgt acctgaggtc agatgtgcaa ggcacgggaa ttccttatac   5340
ttggcagaag aagcggagc cattatgagt cttctcgaac tgcatgtgcc gcatgagact   5400
atctattaca atacgctctt ctcaaacgag atgaaccccc cacagcggca tttcggaccg   5460
accccaacac agtttctgaa ttcagttgtt tataggaatc tacaggcgga ggtaccatgt   5520
aaggatggat ttgtccagga gttccgtcca ttatggagag agaatacaga agaaagcgat   5580
ctgacctcag ataaagcagt gggttacatc acatctgcag tgccctaccg gtctgtatca   5640
ttgctgcact gtgacattga gattcctcca ggatccaatc aaagcttact ggatcaactg   5700
gctaccaatc tgtctctgat tgccatgcat tctgtaaggg agggcggggt cgtgatcatc   5760
aaagtgttgt atgcaatggg atattacttc catctactca tgaacttgtt cactccgtgt   5820
tctacgaaag gatatattct ctctaatggc tatgcatgta gaggggatat ggagtgttac   5880
ctggtatttg tcatgggcta tcgaggtggg cctacatttg tacatgaggt agtgaggatg   5940
gcaaaaactc tagtgcagcg gcacggtaca cttttgtcca aatcagatga gatcacactg   6000
actaggttat ttacctcaca gcggcagcgt gtaacagaca tcctatccag tcctttaccg   6060
agactaataa agttcttgag aaagaatatc gatactgcgc taattgaagc cgggggacaa   6120
cccgtccgtc cattctgtgc agagagcttg gtgaggacac tagcggacac aactcagatg   6180
acccagatca tcgctagtca cattgacaca gtcattcgat ctgtgatcta catggaggct   6240
gagggtgatc tcgccgacac agtgttctta tttacccct acaatctctc tacagacggt   6300
aaaaagagaa catcacttaa acagtgcaca aggcagatct tagaggtcac aatattgggt   6360
cttagagttg aaaatctcaa taaagtaggt gatgtagtca gtctagtact taaaggtatg   6420
atttctctgg aggacctgat ccctctaaga acatacttga agcgtagtac ctgccctaag   6480
tatttgaagt ctgttctagg tattactaaa ctcaaagaaa tgtttacaga cacctcctta   6540
ttatacttga ctcgtgctca acaaaaattc tacatgaaaa ctataggcaa cgcagtcaag   6600
ggatactaca gtaactgtga ctcttaataa gggcccgttt aaacccgctg atcagcctcg   6660
```

```
actgtgccstt ctagttgcca gccatctgtt gtttgcccct cccccgtgcc ttccttgacc    6720
ctggaaggtg ccactcccac tgtcctttcc taataaaatg aggaaattgc atcgcattgt    6780
ctgagtaggt gtcattctat tctgggtggt ggggtggggc aggacagcaa gggggaggat    6840
tgggaagaca atagcaggca tgctggggat gcggtgggct ctatggcttc tgaggcggaa    6900
agaaccagct ggggctctag ggggtatccc cacgcgccct gtagcggcgc attaagcgcg    6960
gcgggtgtgg tggttacgcg cagcgtgacc gctacacttg ccagcgccct agcgcccgct    7020
cctttcgctt tcttcccttc ctttctcgcc acgttcgccg gctttccccg tcaagctcta    7080
aatcgggggc tccctttagg gttccgattt agtgctttac ggcacctcga ccccaaaaaa    7140
cttgattagg gtgatggttc acgtagtggg ccatcgccct gatagacggt ttttcgccct    7200
ttgacgttgg agtccacgtt ctttaatagt ggactcttgt tccaaactgg aacaacactc    7260
aaccctatct cggtctattc ttttgattta agggatttt gccgatttc ggcctattgg    7320 ttaaaaaatg agctgattta acaaaaattt aacgcgaatt aattctgtgg aatgtgtgtc    7380
agttagggtg tggaaagtcc ccaggctccc cagcaggcag aagtatgcaa agcatgcatc    7440
tcaattagtc agcaaccagg tgtggaaagt ccccaggctc cccagcaggc agaagtatgc    7500
aaagcatgca tctcaattag tcagcaacca tagtcccgcc cctaactccg cccatcccgc    7560
ccctaactcc gcccagttcc gcccattctc cgccccatgg ctgactaatt ttttttattt    7620
atgcagaggc cgaggccgcc tctgcctctg agctattcca gaagtagtga ggaggctttt    7680
ttggaggcct aggcttttgc aaaaagctcc cgggagcttg tatatccatt ttcggatctg    7740
atcaagagac aggatgagga tcgtttcgca tgattgaaca agatggattg cacgcaggtt    7800
ctccggccgc ttgggtggag aggctattcg gctatgactg ggcacaacag acaatcggct    7860
gctctgatgc cgccgtgttc cggctgtcag cgcaggggcg cccggttctt tttgtcaaga    7920
ccgacctgtc cggtgccctg aatgaactgc aggacgaggc agcgcggcta tcgtggctgg    7980
ccacgacggg cgttccttgc gcagctgtgc tcgacgttgt cactgaagcg ggaagggact    8040
ggctgctatt gggcgaagtg ccggggcagg atctcctgtc atctcacctt gctcctgccg    8100
agaaagtatc catcatggct gatgcaatgc ggcggctgca tacgcttgat ccggctacct    8160
gcccattcga ccaccaagcg aaacatcgca tcgagcgagc acgtactcgg atggaagccg    8220
gtcttgtcga tcaggatgat ctggacgaag agcatcaggg gctcgcgcca gccgaactgt    8280
tcgccaggct caaggcgcgc atgcccgacg gcgaggatct cgtcgtgacc catggcgatg    8340
cctgcttgcc gaatatcatg gtggaaaatg gccgcttttc tggattcatc gactgtggcc    8400
ggctgggtgt ggcggaccgc tatcaggaca tagcgttggc tacccgtgat attgctgaag    8460
agcttggcgg cgaatgggct gaccgcttcc tcgtgcttta cggtatcgcc gctcccgatt    8520
cgcagcgcat cgccttctat cgccttcttg acgagttctt ctgagcggga ctctgggtt    8580 cgaaatgacc gaccaagcga cgcccaacct gccatcacga tttcgatt ccaccgccgc    8640 cttctatgaa aggttgggct tcggaatcgt tttccgggac gccggctgga tgatcctcca    8700
gcgcggggat ctcatgctgg agttcttcgc ccaccccaac ttgtttattg cagcttataa    8760
tggttacaaa taaagcaata gcatcacaaa tttcacaaat aaagcatttt ttcactgca    8820 ttctagttgt ggtttgtcca aactcatcaa tgtatcttat catgtctgta taccgtcgac    8880
ctctagctag agcttggcgt aatcatggtc atagctgttt cctgtgtgaa attgttatcc    8940
gctcacaatt ccacacaaca tacgagccgg aagcataaag tgtaaagcct ggggtgccta    9000
atgagtgagc taactcacat taattgcgtt gcgctcactg cccgctttcc agtcgggaaa    9060
```

-continued

```
cctgtcgtgc cagctgcatt aatgaatcgg ccaacgcgcg gggagaggcg gtttgcgtat    9120
tgggcgctct tccgcttcct cgctcactga ctcgctgcgc tcggtcgttc ggctgcggcg    9180
agcggtatca gctcactcaa aggcggtaat acggttatcc acagaatcag gggataacgc    9240
aggaaagaac atgtgagcaa aaggccagca aaaggccagg aaccgtaaaa aggccgcgtt    9300
gctggcgttt ttccataggc tccgcccccc tgacgagcat cacaaaaatc gacgctcaag    9360
tcagaggtgg cgaaacccga caggactata aagataccag gcgtttcccc ctggaagctc    9420
cctcgtgcgc tctcctgttc cgaccctgcc gcttaccgga tacctgtccg cctttctccc    9480
ttcgggaagc gtggcgcttt ctcatagctc acgctgtagg tatctcagtt cggtgtaggt    9540
cgttcgctcc aagctgggct gtgtgcacga accccccgtt cagcccgacc gctgcgcctt    9600
atccggtaac tatcgtcttg agtccaaccc ggtaagacac gacttatcgc cactggcagc    9660
agccactggt aacaggatta gcagagcgag gtatgtaggc ggtgctacag agttcttgaa    9720
gtggtggcct aactacggct acactagaag aacagtattt ggtatctgcg ctctgctgaa    9780
gccagttacc ttcggaaaaa gagttggtag ctcttgatcc ggcaaacaaa ccaccgctgg    9840
tagcggtttt tttgtttgca agcagcagat tacgcgcaga aaaaaaggat ctcaagaaga    9900
tcctttgatc ttttctacgg ggtctgacgc tcagtggaac gaaaactcac gttaagggat    9960
tttggtcatg agattatcaa aaaggatctt cacctagatc cttttaaatt aaaaatgaag   10020
ttttaaatca atctaaagta tatatgagta aacttggtct gacagttacc aatgcttaat   10080
cagtgaggca cctatctcag cgatctgtct atttcgttca tccatagttg cctgactccc   10140
cgtcgtgtag ataactacga tacgggaggg cttaccatct ggccccagtg ctgcaatgat   10200
accgcgagac ccacgctcac cggctccaga tttatcagca ataaaccagc cagccggaag   10260
ggccgagcgc agaagtggtc ctgcaacttt atccgcctcc atccagtcta ttaattgttg   10320
ccgggaagct agagtaagta gttcgccagt taatagtttg cgcaacgttg ttgccattgc   10380
tacaggcatc gtggtgtcac gctcgtcgtt tggtatggct tcattcagct ccggttccca   10440
acgatcaagg cgagttacat gatcccccat gttgtgcaaa aaagcggtta gctccttcgg   10500
tcctccgatc gttgtcagaa gtaagttggc cgcagtgtta tcactcatgg ttatggcagc   10560
actgcataat tctcttactg tcatgccatc cgtaagatgc ttttctgtga ctggtgagta   10620
ctcaaccaag tcattctgag aatagtgtat gcggcgaccg agttgctctt gcccggcgtc   10680
aatacgggat aataccgcgc cacatagcag aactttaaaa gtgctcatca ttggaaaacg   10740
ttcttcgggg cgaaaactct caaggatctt accgctgttg agatccagtt cgatgtaacc   10800
cactcgtgca cccaactgat cttcagcatc ttttactttc accagcgttt ctgggtgagc   10860
aaaaacagga aggcaaaatg ccgcaaaaaa gggaataagg gcgacacgga aatgttgaat   10920
actcatactc ttcctttttc aatattattg aagcatttat cagggttatt gtctcatgag   10980
cggatacata tttgaatgta tttagaaaaa taaacaaata ggggttccgc gcacatttcc   11040
ccgaaaagtg ccacctgacg tcgacggatc gggagatctc ccgatcccct atggtgcact   11100
ctcagtacaa tctgctctga tgccgcatag ttaagccagt atctgctccc tgcttgtgtg   11160
ttggaggtcg ctgagtagtg cgcgagcaaa atttaagcta caacaaggca aggcttgacc   11220
gacaattgca tgaagaatct gcttagggtt aggcgttttg cgctgcttcg cgatgtacgg   11280
gccagatata cgcgttgaca ttgattattg actagtyatt aatagtaatc aattacgggg   11340
tcattagttc atagcccata tatggagttc cgcgttacat aacttacggt aaatggcccg   11400
```

-continued

```
cctggctgac cgcccaacga cccccgccca ttgacgtcaa taatgacgta tgttcccata    11460
gtaacgccaa tagggacttt ccattgacgt caatgggtgg agtatttacg gtaaactgcc    11520
cacttggcag tacatcaagt gtatcatatg ccaagtacgc ccctattga cgtcaatgac     11580 ggtaaatggc ccgcctggca ttatgccag tacatgacct tatgggactt tcctacttgg    11640
cagtacatct acgtattagt catcgctatt accatggtga tgcggttttg gcagtacatc    11700
aatgggcgtg gatagcggtt tgactcacgg ggatttccaa gtctccaccc cattgacgtc    11760
aatgggagtt tgttttggca ccaaaatcaa cgggactttc caaaatgtcg taacaactcc    11820
gccccattga cgcaaatggg cggtaggcgt gtacggtggg aggtctatat aagcagagct    11880
ctctggctaa ctagagaacc cactgcttac tggcttatcg aaattaatac gactcactat    11940
agggagaccc aagctggcta gcgtttaaac ttaagcttgg taccgagctc ggatccacta    12000
gtccagtgtg gtggaattct gcagatatcc agcacagtgg c                       12041
```

<210> SEQ ID NO 5
<211> LENGTH: 58
<212> TYPE: DNA
<213> ORGANISM: Artificial Sequence
<220> FEATURE:
<223> OTHER INFORMATION: Forward primer for Segment A

<400> SEQUENCE: 5

```
ccgggcggcc gcgtaatacg actcactata ggaccaaaca gagaatctgt gagttacg     58
```

<210> SEQ ID NO 6
<211> LENGTH: 25
<212> TYPE: DNA
<213> ORGANISM: Artificial Sequence
<220> FEATURE:
<223> OTHER INFORMATION: Reverse primer for Segment A

<400> SEQUENCE: 6

```
ctgtgatatc gcctccatca tagac                                         25
```

<210> SEQ ID NO 7
<211> LENGTH: 25
<212> TYPE: DNA
<213> ORGANISM: Artificial Sequence
<220> FEATURE:
<223> OTHER INFORMATION: Forward primer for Segment B

<400> SEQUENCE: 7

```
cagagcagag ccaagacaat actcc                                         25
```

<210> SEQ ID NO 8
<211> LENGTH: 28
<212> TYPE: DNA
<213> ORGANISM: Artificial Sequence
<220> FEATURE:
<223> OTHER INFORMATION: Reverse primer for Segment B

<400> SEQUENCE: 8

```
cctatctact acatcttgat tggaaccg                                      28
```

<210> SEQ ID NO 9
<211> LENGTH: 51
<212> TYPE: DNA
<213> ORGANISM: Artificial Sequence
<220> FEATURE:
<223> OTHER INFORMATION: Forward primer for Segment C

<400> SEQUENCE: 9
cggcgaattc gcatcatcga gcgcccgcta tagcatggag gccagcacac c    51

<210> SEQ ID NO 10
<211> LENGTH: 32
<212> TYPE: DNA
<213> ORGANISM: Artificial Sequence
<220> FEATURE:
<223> OTHER INFORMATION: Reverse primer for Segment C

<400> SEQUENCE: 10
cggaagctta gataagacgg cctgctgtac gc    32

<210> SEQ ID NO 11
<211> LENGTH: 36
<212> TYPE: DNA
<213> ORGANISM: Artificial Sequence
<220> FEATURE:
<223> OTHER INFORMATION: Forward primer for Segment D

<400> SEQUENCE: 11
cgcggatccg atacaatgac acatgtccag atgagc    36

<210> SEQ ID NO 12
<211> LENGTH: 23
<212> TYPE: DNA
<213> ORGANISM: Artificial Sequence
<220> FEATURE:
<223> OTHER INFORMATION: Reverse primer for Segment D

<400> SEQUENCE: 12
gcaggttgaa tgcgaagaaa tcc    23

<210> SEQ ID NO 13
<211> LENGTH: 27
<212> TYPE: DNA
<213> ORGANISM: Artificial Sequence
<220> FEATURE:
<223> OTHER INFORMATION: Forward primer for Segment E

<400> SEQUENCE: 13
gggtaatcaa gtctacgatg ttgtagc    27

<210> SEQ ID NO 14
<211> LENGTH: 36
<212> TYPE: DNA
<213> ORGANISM: Artificial Sequence
<220> FEATURE:
<223> OTHER INFORMATION: Reverse primer for Segment E

<400> SEQUENCE: 14
ggcgaagctt aagaatgttc attagctcga ttgtgg    36

<210> SEQ ID NO 15
<211> LENGTH: 26
<212> TYPE: DNA
<213> ORGANISM: Artificial Sequence
<220> FEATURE:
<223> OTHER INFORMATION: Forward primer for Segment F

<400> SEQUENCE: 15
ggtgactttg cgagacttga cttagc    26

<210> SEQ ID NO 16
<211> LENGTH: 27
<212> TYPE: DNA

<213> ORGANISM: Artificial Sequence
<220> FEATURE:
<223> OTHER INFORMATION: Reverse primer for Segment F

<400> SEQUENCE: 16
ccaatattgt gacctctaag atctgcc                                      27

<210> SEQ ID NO 17
<211> LENGTH: 29
<212> TYPE: DNA
<213> ORGANISM: Artificial Sequence
<220> FEATURE:
<223> OTHER INFORMATION: Forward primer for Segment G1

<400> SEQUENCE: 17
agagaacatc acttaaacag tgcacaagg                                    29

<210> SEQ ID NO 18
<211> LENGTH: 37
<212> TYPE: DNA
<213> ORGANISM: Artificial Sequence
<220> FEATURE:
<223> OTHER INFORMATION: Reverse primer for Segment G1

<400> SEQUENCE: 18
ccatgccgac ccaccaaaca aagatttggt gaatgac                           37

<210> SEQ ID NO 19
<211> LENGTH: 134
<212> TYPE: DNA
<213> ORGANISM: Artificial Sequence
<220> FEATURE:
<223> OTHER INFORMATION: First forward primer for Segment G2

<400> SEQUENCE: 19
ttcaccaaat ctttgtttgg tgggtcggca tggcatctcc acctcctcgc ggtccgacct    60
gggcatccga aggaggacgc acgtccactc ggatggctaa gggaggggca ctccgcggtc   120
actgctaaca aagc                                                    134

<210> SEQ ID NO 20
<211> LENGTH: 138
<212> TYPE: DNA
<213> ORGANISM: Artificial Sequence
<220> FEATURE:
<223> OTHER INFORMATION: First reverse primer for Segment G2

<400> SEQUENCE: 20
cctgacgtcg acagctccag caaaaaaccc ctcaagaccc gtttagaggc cccaaggggt    60
tatgctagtt attgctcagc ggtggcagca gccaactcag cttcctttcg ggctttgtta   120
gcagtgaccg cggagtgc                                                138

<210> SEQ ID NO 21
<211> LENGTH: 24
<212> TYPE: DNA
<213> ORGANISM: Artificial Sequence
<220> FEATURE:
<223> OTHER INFORMATION: Second forward primer for Segment G2

<400> SEQUENCE: 21
ttcaccaaat ctttgtttgg tggg                                         24

<210> SEQ ID NO 22
<211> LENGTH: 21

```
<212> TYPE: DNA
<213> ORGANISM: Artificial Sequence
<220> FEATURE:
<223> OTHER INFORMATION: Second reverse primer for Segment G2

<400> SEQUENCE: 22
cctgacgtcg acagctccag c                                              21
```